(12) United States Patent
Hignight et al.

(10) Patent No.: US 11,800,837 B2
(45) Date of Patent: *Oct. 31, 2023

(54) AMERICAN RYEGRASS APMT 005, A NEW TURFGRASS

(71) Applicants: Kenneth Hignight, Jefferson, OR (US); Debra Hignight, Jefferson, OR (US)

(72) Inventors: Kenneth Hignight, Jefferson, OR (US); Debra Hignight, Jefferson, OR (US)

(73) Assignee: NexGen Turf Research, LLC, Albany, OR (US)

( * ) Notice: Subject to any disclaimer, the term of this patent is extended or adjusted under 35 U.S.C. 154(b) by 394 days.

This patent is subject to a terminal disclaimer.

(21) Appl. No.: 16/917,136

(22) Filed: Jun. 30, 2020

(65) Prior Publication Data
US 2020/0337253 A1  Oct. 29, 2020

Related U.S. Application Data

(62) Division of application No. 16/158,068, filed on Oct. 11, 2018, now Pat. No. 10,721,879.

(60) Provisional application No. 62/570,988, filed on Oct. 11, 2017.

(51) Int. Cl.
| | |
|---|---|
| *A01H 5/12* | (2018.01) |
| *A01H 6/46* | (2018.01) |
| *A01G 20/00* | (2018.01) |
| *A01C 14/00* | (2006.01) |

(52) U.S. Cl.
CPC ............... *A01G 20/00* (2018.02); *A01H 5/12* (2013.01); *A01H 6/46* (2018.05); *A01H 6/463* (2018.05); *A01C 14/00* (2013.01)

(58) Field of Classification Search
CPC .......... A01G 20/00; A01H 6/46; A01H 6/463; A01H 5/12; A01C 14/00
USPC ......................................... 800/320; Plt./388
See application file for complete search history.

(56) References Cited

U.S. PATENT DOCUMENTS 10,721,879 B2 *  7/2020  Hignight ................ A01G 20/00

OTHER PUBLICATIONS

Joanna Majka et al. Karyotype reshufflings of Festuca pratensis × Lolium perenne hybrids. Prtoplasma (2018) 255; 451-458. Published on line Sep. 7, 2017.*
Banfi et al., "From Schedonorus and Micropyropsis to Lolium (Poaceae: Ioliinae): New combinations and typifications", Taxon, Jun. 1, 2017, pp. 708-717, vol. 66, No. 3.
Boller et al., "Fodder Crops and Amenity Grasses", Handbook of Plant Breeding, 2010, vol. 5, Publisher: Springer.
Hopkins et al., "Breeding, Genetics, and Cultivars", Tall Fescue for the Twenty-first Century, 2009, vol. Chapter 19, No. 339-386.

* cited by examiner

*Primary Examiner* — June Hwu
(74) *Attorney, Agent, or Firm* — Dentons Davis Brown; Matthew Coryell; Kassandra Ricklefs

(57) ABSTRACT

A new turfgrass APMT 005 (ATCC Accession No. PTA-126634). A method of over-seeding dormant warm season grasses, including over-seeding the warm season grass with Turf Type *Festulolium* (American Ryegrass) such that the American Ryegrass will provide a green cover during the winter months but will die out when the temperatures increase to the point which allow the warm-season grass to regrow. A method to maintain green coverage of turf year-round including planting a warm season grass, and over-seeding the warm season grass with American Ryegrass. The method where the American Ryegrass is APMT005.

3 Claims, 1 Drawing Sheet

Table 19. Drought Data from Albany, OR (N=100 entries)

| Cultivar | Percent Green Cover |
|---|---|
| APMT003 | 29.70 |
| APMT005 | 18.75 |
| APMT006 | 18.59 |
| AMFT118 | 16.61 |
| APMT004 | 16.16 |
| APMT008 | 9.98 |
| APR2931 | 9.81 |
| APMT007 | 7.56 |
| AMF117 | 7.41 |
| Soprano | 7.16 |
| Manhattan 6 | 5.26 |
| APR2936 | 4.96 |
| APR2916 | 4.86 |
| APRT2114 | 3.56 |
| Pizzazz 2 | 2.39 |
| Pop | 1.90 |
| CV | 89.95 |
| LSD (0.05) | 9.59 |
| GRAND MEAN | 7.90 |
| MIN. MEAN | 1.87 |
| MAX. MEAN | 29.70 |

AMERICAN RYEGRASS APMT 005, A NEW TURFGRASS

CROSS REFERENCE TO RELATED APPLICATIONS

This application is a divisional of U.S. patent application Ser. No. 16/158,068, filed Oct. 11, 2018, and entitled "A Method of Over-Seeding Using American Ryegrass, A New Turfgrass," which claims priority to U.S. Provisional Application No. 62/570,988, filed Oct. 11, 2017 and entitled "A METHOD OF OVER-SEEDING USING AMERICAN RYEGRASS, A NEW TURFGRASS," each of which are hereby incorporated by reference in its entirety.

BACKGROUND OF THE INVENTION

1. Field of the Invention

The present invention relates generally to a new turfgrass denominated American turfgrass and, more specifically, to a method of using American turfgrass for overseeding.

This American ryegrass [x *Festulolium braunii* (K. Richt.) A. *Camus*] invention relates to cultivated varieties of true breeding, stable, tetraploid hybrid between *Festuca pratensis* Huds. X *Lolium perenne* L., for the novel use as 1) a short lived, improved turfgrass on golf courses, athletic fields, lawns, and other areas using seeded turfgrasses; 2) over-seeding of dormant warm season grasses since its lack of heat tolerance (in southern US) allows for a smooth transition for the warm-season grass; and 3) provide a permanent turf more with cold tolerance, with good winter color, and better drought tolerance than perennial ryegrass.

2. Background of the Art

*Festulolium* is the name for intergeneric/interspecific hybrid grasses developed by crossing species of *Festuca* and *Lolium*. This enables combining the best properties of the two types of grass. Table 1 shows the resulting *Festulolium* hybrids, their complex, diverse, taxonomy, and nomenclature (Banfi et al, 2017; Ghesquiere et al., 2010; Hopkins et al., 2009). Here forward the forage hybrids are referred to as only *Festulolium*. The novel turf type *Festulolium* invention will be referred to as American Ryegrass or turf type *Festulolium*.

TABLE 1

| Parent | Parent | Traditional Classification Scientific Name | Current Classification based on Banfi et al. (2017) Scientific Name |
|---|---|---|---|
| *Festuca apennina* (*Lolium apenninum*) | *Festuca gigantea* (*Lolium gignanteum*) | *Festuca xczarnohorensis* Zapał. | *Lolium xczarnohorense* (Zapał.) Banfi, Galasso, Foggi, Kopecký & Ardenghi |
| *Festuca arundinacea* (*Lolium rundinaceum*) | *Festuca pratensis* (*Lolium pratense*) | *Festuca xaschersoniana* Dörfl. | *Lolium xaschersonianum* (Dörfl.) Banfi, Galasso, Foggi, Kopecký & Ardenghi |
| *Festuca arundinacea* (*Lolium rundinaceum*) | *Festuca gigantea* (*Lolium gignanteum*) | *Festuca xfleischeri* | *Lolium xfleischeri* (Rohlena) Banfi, Galasso, Foggi, Kopecký & Ardenghi |
| *Festuca arundinacea* (*Lolium rundinaceum*) | *Lolium perenne* | x*Festulolium holmbergii* (Dörfl.) P. Fourn. | *Lolium holmbergii* (Dörfl.) Banfi, Galasso, Foggi, Kopecký & Ardenghi |
| *Festuca arundinacea* (*Lolium rundinaceum*) | *Lolium multiflorum* Lam. | x*Schedolium krasanii* H. Scholz | *Lolium xkrasanii* (H. Scholz), Banfi, Galasso, Foggi, Kopecký & Ardenghi [a] |
| *Festuca gigantea* (*Lolium gignanteum*) | *Lolium perenne* | x*Festulolium brinkmannii* (A. Braun) Asch. & Graebn. | *Lolium xbrinkmannii* (A. Braun) Banfi, Galasso, Foggi, Kopecký & Ardenghi |
| *Festuca gigantea* (*Lolium gignanteum*) | *Festuca pratensis* (*Lolium pratense*) | *Festuca xschlickumii* Grantzow | *Lolium xschlickumii* (Grantzow) Banfi, Galasso, Foggi, Kopecký & Ardenghi |
| *Festuca gigantea* (*Lolium gignanteum*) | *Lolium multiflorum* | "x*Festulolium nilssonii*" Cugnac & A. Camus in Bull. Soc. Bot. France 91: 19. 1944, nom. nud. (Art. 39.1 of the ICN) | "x*Festulolium nilssonii*" Cugnac & A. Camus in Bull. Soc. Bot. France 91: 19. 1944, nom. nud. (Art. 39.1 of the ICN) [b] |
| *Festuca heterophylla* Lam. | *Festuca pratensis* (*Lolium pratense*) | x*Festulolium wippraense* (Wein) Banfi, Galasso, Foggi, Kopecký & Ardenghi, | x*Festulolium wippraense* (Wein) Banfi, Galasso, Foggi, Kopecký & Ardenghi, |
| *Festuca ovina* L. | *Festuca pratensis* (*Lolium pratense*) | *Festuca xpseudofallax* Wein | x*Festulolium pseudofallax* (Wein) Banfi, Galasso, Foggi, Kopecký & Ardenghi |
| *Festuca pratensis* (*Lolium pratense*) | *Lolium temulentum* | x*Festulolium colinii* Cugnac & A. Camus ex A. Camus | x*Festulolium colinii* Cugnac & A. Camus ex A. Camus |
| *Festuca pratensis* (*Lolium pratense*) | *Lolium perenne* | x*Festulolium braunii* (K. Richt.) A. Camus (1927) x *Festulolium loliaceum*(Huds.) P. Fourn (1935) | *Lolium xelongatum* (Ehrh.) Banfi, Galasso, Foggi, Kopecký & Ardenghi [c] |
| *Festuca pratensis* (*Lolium* | *Lolium multiflorum* | *Festuca xsubnutans* Holmb. | *Lolium xsubnutans* (Holmb.) |

TABLE 1-continued

| Parent | Parent | Traditional Classification Scientific Name | Current Classification based on Banfi et al. (2017) Scientific Name |
|---|---|---|---|
| pratense) | | | Banfi, Galasso, Foggi, Kopecký & Ardenghi (2017) [Lolium multiflorum Lam. × L. pratense (Huds.) Darbysh.] ≡ Festuca ×subnutans Holmb. in Bot. Not. 1930: 94. 1930 - Type: not designated.[d] |
| Festuca rubra | Festuca pratensis (Lolium pratense) | Festuca ×hercynica Wein | Festulolium ×hercynicum (Wein) Banfi, Galasso, Foggi, Kopecký & Ardenghi |
| Festuca rubra | Lolium perenne | "×Festulolium frederici" Cugnac & A. Camus in Bull. Soc. Bot. France 91: 19. 1944, nom. nud. (Art. 39.1 of the ICN) | "×Festulolium frederici" Cugnac & A. Camus in Bull. Soc. Bot. France 91: 19. 1944, nom. nud. (Art. 39.1 of the ICN)[e] |

[a] "×Fesutulolium pabulare"; an invalid name of uncertain origin.
[b] "×Festulolium nilssonii" Cugnac & A. Camus is based on a previous description in German (without name) by Nilsson (1930), thus it is not validly published (Art. 39.1 of the ICN). It is an artificial hybrid (Nilsson, 1930).
[c] ×Festulolium braunii (K. Richt.) A. Camus; Festuca × braunii K. Richt., based on F. loliacea var.; aristata A. Braun ex Döll, is a short-awned form of Lolium × elongatum, erroneously considered as a hybrid between L. multiflorum and L. pratense; the correct name of the latter is L. × subnutans (Holmberg, 1930).
[d] ×Festulolium braunii (K. Richt.) A. Camus; Festuca × braunii K. Richt., based on F. loliacea var.; aristata A. Braun ex Döll, is a short-awned form of Lolium × elongatum, erroneously considered as a hybrid between L. multiflorum and L. pratense; the correct name of the latter is L. × subnutans (Holmberg, 1930).
[e] "×Festulolium frederici" Cugnac & A. Camus is based on a previous description in German (without name) by Nilsson (1933), thus it is not validly published (Art. 39.1 of the ICN). It is a spontaneous hybrid (Nilsson, 1933). This plant is reported by Stace (2010) to be known in the wild only from Sweden; previous records from Great Britain are erroneous (Banfi et al. 2017).

Historically and traditionally, *Festulolium* cultivars have only been developed for forage qualities (Ghesquiere et al., 2010; Hopkins et al., 2009). Table 2 presents some of the released cultivars of *Festulolium* and their pedigree. In forages, the fescues contribute qualities such as high dry matter yield, resistance to cold, drought tolerance and persistence, while ryegrass is characterized by rapid establishment, good spring growth, good digestibility, sugar content and palatability. The individual *Festulolium* cultivars contain various combinations of these qualities, but all are substantially higher yielding than their parent lines. While *Festulolium* have been around for many years as forage and fodder, there are no commercially available cultivars of *Festulolium* available for permanent or overseeding turf use. This is the first time turf type *Festulolium* cultivars have been developed specifically for turf applications.

TABLE 2

| | Pedigree | | |
|---|---|---|---|
| Cultivar | Parent | Parent | Use |
| Becva | Festuca (Lolium) arundinacea × | Lolium multiflorum | Forage |
| Felina | Festuca (Lolium) arundinacea × | Lolium multiflorum | Forage |
| Felovia | Festuca (Lolium) arundinacea × | Lolium multiflorum | Forage |
| Fojtan | Festuca (Lolium) arundinacea × | Lolium multiflorum | Forage |
| Hykor | Festuca (Lolium) arundinacea × | Lolium multiflorum | Forage |
| Johnstone | Festuca (Lolium) arundinacea × | Lolium multiflorum | Forage |
| Kenhy | Festuca (Lolium) arundinacea × | Lolium multiflorum | Forage |
| Korina | Festuca (Lolium) arundinacea × | Lolium multiflorum | Forage |
| KY2N56 | Festuca (Lolium) arundinacea × | Lolium multiflorum | Forage |
| Lesana | Festuca (Lolium) arundinacea × | Lolium multiflorum | Forage |
| Lofa | Festuca (Lolium) arundinacea × | Lolium multiflorum | Forage |
| Mahulena | Festuca (Lolium) arundinacea × | Lolium multiflorum | Forage |
| Puga | Festuca (Lolium) arundinacea × | Lolium multiflorum | Forage |
| Vetra | Festuca (Lolium) arundinacea × | Lolium multiflorum | Forage |
| Achilles | Festuca (Lolium) pratensis × | Lolium multiflorum | Forage |
| Agula | Festuca (Lolium) pratensis × | Lolium multiflorum | Forage |
| Elmet | Festuca (Lolium) pratensis × | Lolium multiflorum | Forage |
| Emrys | Festuca (Lolium) pratensis × | Lolium multiflorum | Forage |
| Felopa | Festuca (Lolium) pratensis × | Lolium multiflorum | Forage |
| Festum | Festuca (Lolium) pratensis × | Lolium multiflorum | Forage |
| Hostyn | Festuca (Lolium) pratensis × | Lolium multiflorum | Forage |
| Lifema | Festuca (Lolium) pratensis × | Lolium multiflorum | Forage |
| Paulena | Festuca (Lolium) pratensis × | Lolium multiflorum | Forage |
| Paulito | Festuca (Lolium) pratensis × | Lolium multiflorum | Forage |
| Perseus | Festuca (Lolium) pratensis × | Lolium multiflorum | Forage |
| Perun | Festuca (Lolium) pratensis × | Lolium multiflorum | Forage |
| Punia DS | Festuca (Lolium) pratensis × | Lolium multiflorum | Forage |

TABLE 2-continued

| Cultivar | Pedigree | | | Use |
|---|---|---|---|---|
| | Parent | | Parent | |
| Rakopan | *Festuca (Lolium) pratensis* | x | *Lolium multiflorum* | Forage |
| Sulino | *Festuca (Lolium) pratensis* | x | *Lolium multiflorum* | Forage |
| Tatay II | *Festuca (Lolium) pratensis* | x | *Lolium multiflorum* | Forage |
| Banka | *Festuca (Lolium) pratensis* | x | *Lolium perenne* | Forage |
| Barfest | *Festuca (Lolium) pratensis* | x | *Lolium perenne* | Forage |
| Duo | *Festuca (Lolium) pratensis* | x | *Lolium perenne* | Forage |
| FuRs9806 | *Festuca (Lolium) pratensis* | x | *Lolium perenne* | Forage |
| Gibrid | *Festuca (Lolium) pratensis* | x | *Lolium perenne* | Forage |
| Kaibanka | *Festuca (Lolium) pratensis* | x | *Lolium perenne* | Forage |
| Kemal | *Festuca (Lolium) pratensis* | x | *Lolium perenne* | Forage |
| Matrix | *Festuca (Lolium) pratensis* | x | *Lolium perenne* | Forage |
| Prior | *Festuca (Lolium) pratensis* | x | *Lolium perenne* | Forage |
| Saikava | *Festuca (Lolium) pratensis* | x | *Lolium perenne* | Forage |
| Spring Green | *Festuca (Lolium) pratensis* | x | *Lolium perenne* | Forage |
| Theophano | *Festuca (Lolium) pratensis* | x | *Lolium perenne* | Forage |
| Evergreen | *Festuca (Lolium) pratensis* | x | *Lolium multiflorum* | Forage |
| Kemal | *Festuca (Lolium) pratensis* | x | *Lolium multiflorum* | Forage |
| Tandem | *Festuca (Lolium) pratensis* | x | *Lolium multiflorum* | Forage |
| Lueur | *Lolium multiflorum* | x | *Festuca glaucescens* | Forage |
| Lusilium | *Lolium multiflorum* | x | *Festuca glaucescens* | Forage |
| Luxane | *Lolium multiflorum* | x | *Festuca glaucescens* | Forage |

A stable cultivar of American Ryegrass would be a desirable grass for use in both 1) overseeding of dormant warm season grasses; and 2) permanent turf in more temperate climates.

A turf type *Festulolium* would be a desirable grass for use in overseeding of dormant warm season grasses, since its lack of heat tolerance allows for a smooth transition for the warm-season grass. *Festulolium* will provide a green cover during the winter months but will die out when the temperatures increase which allow the warm-season grass to grow.

For many southern golf courses planted with Bermuda grass, a standard practice is to overseed every fall with diploid perennial ryegrass. Diploid perennial ryegrass provides an outstanding turf cover during the cool winter months. However, diploid perennial ryegrass is very persistent and does not easily die out and give way for the re-emerging Bermuda grass in the spring when warm weather returns.

Turfgrass managers could utilize a cultivar that has a dark green color, rapid establishment, and the ability to transition rapidly. The two most widely used species for overseeding are annual and diploid perennial ryegrass. Annual ryegrass, such as the variety 'Gulf,' have an undesirable color and a very rapid vertical extension rate which results in frequent mowing. Diploid perennial ryegrass has been developed for heat tolerance and permanent turf use and therefore does not transition well.

American Ryegrass in more temperate climates will provide a permanent turf more cold tolerance, with good winter color, and better drought tolerance and persistence than perennial ryegrass.

SUMMARY OF THE INVENTION

Turf type *Festulolium* cultivars (including, but not exclusive to) known as breeder's codes: AMPT001; AMPT002; AMPT003; AMPT005; AMPT006; AMPT007; AMPT008; AMPT009; AMPT010; and AMPT011, and methods used to produce the grass are provided. The grass is useful as a short lived, improved turfgrass on golf courses, athletic fields, lawns and other areas using seeded turfgrasses. The grass is also useful in overseeding of dormant warm season grasses since its lack of heat tolerance allows for a smooth transition for the warm-season grass. Turf type *Festulolium* will provide a green cover during the winter months but will die out when the temperatures increases to the point which allow the warm-season grass to grow. Turf type *Festulolium*, in more temperate climates, will provide a permanent turf more cold tolerance, with good winter color, and better drought tolerance and persistence than perennial ryegrass.

Turf type *Festulolium* cultivars of the present invention are different from all other known *Festulolium* cultivars in that they have the following characteristics:

TABLE 3

| CULTIVAR | Mature Plant Height (cm) | Flag Leaf Height (cm) | Leaf Blade Height (cm) | Panicle Length (cm) | Flag Leaf Length (cm) | Flag Leaf Sheath Length (cm) | Leaf Blade Length (cm) |
|---|---|---|---|---|---|---|---|
| American Ryegrass | 92.140 | 58.015 | 38.783 | 49.392 | 35.628 | 16.030 | 34.117 |
| CV | 16.857 | 21.476 | 30.402 | 17.227 | 20.372 | 26.906 | 19.526 |
| LSD | 4.695 | 3.727 | 3.250 | 2.738 | 2.191 | 1.420 | 1.961 |
| Minimum | 76.332 | 48.667 | 22.835 | 44.203 | 29.817 | 15.253 | 27.085 |
| Maximum | 98.873 | 62.908 | 42.158 | 69.403 | 40.530 | 25.235 | 34.838 |

TABLE 3

| CULTIVAR | Leaf Blade Sheath Length (cm) | Flag Leaf Width (mm) | Leaf Blade Width (mm) | Lemma Length (mm) | Lemma Width (mm) | Glume Length (mm) | Spike Length (cm) | Spikelet Length (mm) |
|---|---|---|---|---|---|---|---|---|
| American Ryegrass | 9.893 | 4.65 | 5.08 | 7.847 | 1.782 | 10.950 | 24.728 | 16.218 |
| CV | 24.157 | 28.30 | 24.34 | 9.507 | 15.695 | 17.124 | 17.643 | 16.463 |
| LSD | 0.763 | 0.42 | 0.37 | 0.222 | 0.081 | 0.493 | 1.286 | 0.792 |
| Minimum | 8.930 | 4.05 | 3.97 | 7.328 | 1.517 | 5.102 | 21.060 | 14.307 |
| Maximum | 13.468 | 5.48 | 5.68 | 8.073 | 1.835 | 10.950 | 26.452 | 16.832 |

BRIEF DESCRIPTION OF THE DRAWINGS

FIG. 1 is a table showing drought data from Albany, Oreg.

DETAILED DESCRIPTION

As used in the broad context in grasses, the term "overseeding" relates to the process of placing grass seed over an existing stand of turfgrass.

As used in the context of this document, the term "overseeding" relates only to the use of cool-season grasses sown into an existing warm season grass turf, for the purpose of having a green cover during the winter months when the warm-season grass is dormant.

As used in the context of this document, the term "permanent turf" relates to temperate climates in which in invention is more cold tolerant, with good winter color, spring green-up, and better drought tolerance and persistence than perennial ryegrass Key Elements in Overseeding Turfgrass Establishment—It is important in an overseeding grass to have rapid establishment. This includes a quick germination of the seed and the ability to tiller into areas adjacent to the next seedling.

Color—Many users of overseeding grasses prefer a dark green color. A light color grass can be made darker by applying iron. However, the user generally prefers to not do this unless the grass is too light in color.

Transition—A desirable transition grass is one that will die completely when the warm season grass is starting to reach its peak performance. The overseeding grass cannot die too quickly in the spring before the warm-season grass has an opportunity to grow.

Discussion of Current Species Used

Annual ryegrass—Annual ryegrass was used extensively for overseeding prior to 1970. With breeding improvements of perennial ryegrass the use of annual ryegrass has declined. Annual ryegrass has an excellent germination rate but lacks tillering ability. Annual ryegrass is light in color and usually transitions too abruptly. The course leaf texture and very fast growth rate are undesirable.

Diploid Perennial ryegrass—Perennial ryegrass has a quick germination. It germinates slower than annual ryegrass but still within an acceptable range for the user. It has a very good tillering ability but in some cases it is too aggressive resulting in damage to the warm season grass. Newer cultivars of perennial ryegrass have excellent, dark green, color. The newer varieties of perennial ryegrass which are being sold as overseeding grasses were developed for permanent turf use. The result is a poor transitioning ability. This has resulted in the use of chemical applications to remove the perennial ryegrass. When this is necessary the turf has damage for several weeks, until the warm-season grass can recover.

Intermediate ryegrass—Intermediate ryegrass performance is more difficult to predict. It is a cross between annual and perennial ryegrass. If only one cross is made the performance is most similar to annual ryegrass. Each successive backcross to perennial ryegrass results in performance similar to diploid perennial ryegrass. A problem with current intermediate ryegrass is that it often transitions too rapidly, before the warm-season grass has a desirable level of performance.

*Poa trivialis* and Fine fescues—Both of these have slow germination and establishment. Because of this they are commonly used in mixtures with other grasses. The cost of producing these grasses is higher and as a result they are not usually used alone. The fine fescues have good transitioning ability compared to *Poa trivialis*.

American Ryegrass—has a rich very dark green color, high tiller density and slow vertical growth rate. All previous *Festulolium* cultivars have been developed for forage use, and therefore have a light color, poor turf density, and a rapid vertical growth rate. American Ryegrass has a rapid germination and establishment rate, and transitions when used in overseeding with Bermuda grass (warm-season). American Ryegrass transitions better than diploid perennial ryegrass. American Ryegrass in more temperate climates, will provide a permanent turf more cold tolerance, with good winter color, and better drought tolerance and persistence than perennial ryegrass.

TABLE 4

| Species Used | Establishment | Color | Transition in warm season grasses |
|---|---|---|---|
| Annual ryegrass | E | P | E |
| American Ryegrass | E | E | E |
| Diploid Perennial ryegrass | VG | E | P-F |
| *Poa trivialis* | F | P | F |
| Intermediate ryegrass | VG | F-G | G |
| Meadow fescue | VG | G | E |

E—excellent;
VG—very good;
F—fair;
P—poor

Morphological descriptors for American Ryegrass (Turf type *Festulolium*) can be found in Tables 5A-E, wherein the following definitions are used:

1. Genetic Color—the measure of the amount of lightness or darkness of green color. Recorded as a 1-9 subjective rating where 9=dark;

2. Growth Habit—the degree of erectness of a single plant. 1=prostrate (flat), 2=semi-prostrate, 3=horizontal, 7=semi-erect, 9=erect;
3. Inflorescence—the flowering portion of a grass plant (in ryegrass the inflorescence is a spike);
4. Spike Length—measured from the upper most node to the apex of the inflorescence;
5. Node—the joint on a grass culm; A swollen region on the stem;
6. Leaf Blade—the flattened portion of a grass leaf located above the leaf sheath;
7. Leaf Blade Length—the length of the leaf blade; Measured on the first leaf subtending the flag leaf in cm;
8. Leaf Blade Width—measure of the width of the first blade subtending the flag leaf in mm taken 1 cm from the collar;
9. Leaf Blade Height—the height of the leaf blade from the ground to the collar in cm;
10. Leaf Sheath Length—the length of the leaf sheath. Measured on the first leaf subtending the flag leaf in cm.;
11. Flag Leaf—the first leaf blade subtending the inflorescence;
12. Flag Leaf Length—the total length of a flag leaf which includes the sheath and blade. Measured from the uppermost node to the end of the upper most blade in cm.;
13. Flag Leaf Width—the measure of the width of the flag leaf blade taken 1 cm from the collar of the flag leaf in mm.;
14. Flag Leaf Height—the height of the flag leaf, measured from the ground to the collar of the flag leaf in cm.;
15. Flag Leaf Sheath Length—the sheath length of the flag leaf, measured from the node to the collar in cm.;
16. Mature Plant Height—the height in cm of a mature plant from the ground to the apex of a mature inflorescence
17. Glume—the first pair of bracts at the base of a spikelet;
18. Spikelet—the basic unit of a grass inflorescence, includes glumes, lemmas, paleas and reproductive organs;
19. Floret—the portion of the spikelet that may include lemma, palea and reproductive organs;
20. Lemma—an odd veined bract above the glumes.
21. Palea—the 0—two veined bract above the glumes and lemma, subtending the reproductive organs;
22. Seed Size—the relative size of seeds usually measured by determining the number of seeds per pound;
23. 1000—seed weight—the weight of 1,000 whole seeds;
24. Turfgrass Density—the number of tillers per unit area of a turfgrass sward;
25. Turf—a covering of mowed vegetation usually a grass;
26. Turfgrass—a species or cultivar of grass that is a mowed turf;
27. Turf Color—a visual and digital analysis score of the turfgrass community, when visual the color is measured on a scale of 1-9 with 9 being dark; and
28. Turf Quality—the degree to which a turf conforms to a standard of uniformity, density, texture, growth habit, color and is generally taken as subjective data on a 1-9 scale with 9 being the best quality.

TABLE 5A

| CULTIVAR | Heading Date Julian Days | | Anthesis Date Julian Days | |
|---|---|---|---|---|
| | 2015 | 2016 | 2015 | 2016 |
| AMFT114 | 127.67 | 126.00 | 147.33 | 141.67 |
| APRT2344 | 134.67 | 129.00 | 153.33 | 150.33 |
| APMT002 | 134.33 | 128.67 | 152.00 | 148.67 |
| APMT003 | 136.00 | 129.67 | 154.33 | 149.00 |
| APMT004 | 133.33 | 127.33 | 151.33 | 147.67 |
| APMT005 | 135.00 | 129.33 | 152.67 | 151.00 |
| CV | 2.15 | 1.76 | 1.36 | 1.42 |
| LSD (0.05) | 2.37 | 0.97 | 1.87 | 1.20 |
| GRAND MEAN | 133.50 | 128.33 | 151.83 | 148.06 |
| MIN. MEAN | 127.67 | 126.00 | 147.33 | 141.67 |
| MAX. MEAN | 136.00 | 129.67 | 154.33 | 151.00 |

TABLE 5B

| CULTIVAR | Plant Width (cm) | | Mature Plant Height (cm) | | Flag Leaf Height (cm) | | Leaf Blade Height (cm) | |
|---|---|---|---|---|---|---|---|---|
| | 2015 | 2016 | 2015 | 2016 | 2015 | 2016 | 2015 | 2016 |
| AMFT114 | 23.767 | 21.900 | 96.767 | 108.633 | 55.333 | 64.500 | 22.833 | 32.533 |
| APRT2344 | 30.333 | 24.600 | 76.333 | 74.900 | 48.667 | 44.967 | 29.033 | 29.100 |
| APMT002 | 33.233 | 25.800 | 98.867 | 86.700 | 61.733 | 53.267 | 41.333 | 36.400 |
| APMT003 | 33.633 | 26.533 | 92.733 | 80.933 | 59.233 | 49.400 | 38.867 | 31.933 |
| APMT004 | 31.367 | 24.600 | 98.133 | 84.100 | 62.900 | 53.000 | 42.167 | 35.667 |
| APMT005 | 31.833 | 26.667 | 92.167 | 82.500 | 58.033 | 51.567 | 38.767 | 34.500 |
| CV | 6.663 | 6.194 | 6.175 | 4.208 | 8.463 | 4.955 | 12.324 | 7.116 |
| LSD (0.05) | 3.027 | 2.293 | 8.452 | 5.373 | 7.220 | 3.870 | 6.475 | 3.513 |
| GRAND MEAN | 30.694 | 25.017 | 92.500 | 86.294 | 57.650 | 52.783 | 35.500 | 33.356 |
| MIN. MEAN | 23.767 | 21.900 | 76.333 | 74.900 | 48.667 | 44.967 | 22.833 | 29.100 |
| MAX. MEAN | 33.633 | 26.667 | 98.867 | 108.633 | 62.900 | 64.500 | 42.167 | 36.400 |

TABLE 5C

| CULTIVAR | Panicle Length (cm) 2015 | 2016 | Flag Leaf Length (cm) 2015 | 2016 | Flag Leaf Sheath Length (cm) 2015 | 2016 | Flag Leaf Internode Length (cm) 2015 | 2016 |
|---|---|---|---|---|---|---|---|---|
| AMFT114 | 69.433 | 71.400 | 40.567 | 41.967 | 25.233 | 27.567 | 20.100 | 19.033 |
| APRT2344 | 44.200 | 43.533 | 29.800 | 30.033 | 15.567 | 14.067 | 14.167 | 8.900 |
| APMT002 | 51.867 | 47.767 | 38.067 | 34.400 | 16.267 | 15.500 | 14.233 | 10.067 |
| APMT003 | 49.233 | 45.833 | 36.367 | 33.700 | 15.600 | 14.233 | 14.867 | 9.800 |
| APMT004 | 51.500 | 45.667 | 34.833 | 32.433 | 15.233 | 14.667 | 15.267 | 9.567 |
| APMT005 | 49.400 | 47.367 | 35.633 | 34.033 | 16.033 | 15.067 | 13.700 | 9.767 |
| CV | 4.532 | 4.480 | 7.075 | 4.517 | 7.322 | 4.474 | 10.047 | 3.942 |
| LSD (0.05) | 3.528 | 3.332 | 3.757 | 2.301 | 1.877 | 1.116 | 2.288 | 0.653 |
| GRAND MEAN | 52.606 | 50.261 | 35.878 | 34.428 | 17.322 | 16.850 | 15.389 | 11.189 |
| MIN. MEAN | 44.200 | 43.533 | 29.800 | 30.033 | 15.233 | 14.067 | 13.700 | 8.900 |
| MAX. MEAN | 69.433 | 71.400 | 40.567 | 41.967 | 25.233 | 27.567 | 20.100 | 19.033 |

TABLE 5D

| CULTIVAR | Leaf Blade Length (cm) 2015 | 2016 | Leaf Sheath Length (cm) 2015 | 2016 | Flag Leaf Width (mm) 2015 | 2016 | Leaf Blade Width (mm) 2015 | 2016 |
|---|---|---|---|---|---|---|---|---|
| AMFT114 | 34.733 | 38.533 | 13.467 | 19.700 | 5.00 | 7.67 | 5.33 | 9.00 |
| APRT2344 | 27.100 | 29.367 | 8.900 | 11.633 | 4.33 | 5.33 | 4.00 | 5.00 |
| APMT002 | 34.833 | 33.633 | 10.200 | 12.967 | 5.33 | 6.33 | 5.67 | 6.67 |
| APMT003 | 34.533 | 32.167 | 10.133 | 12.733 | 5.33 | 5.67 | 5.00 | 6.00 |
| APMT004 | 34.867 | 30.900 | 10.100 | 13.167 | 5.00 | 6.00 | 5.00 | 6.67 |
| APMT005 | 34.133 | 34.067 | 9.900 | 12.667 | 4.67 | 6.00 | 5.00 | 6.00 |
| CV | 6.180 | 4.517 | 6.591 | 4.484 | 9.53 | 9.36 | 8.94 | 5.33 |
| LSD (0.05) | 3.052 | 2.213 | 1.019 | 0.917 | 0.70 | 0.85 | 0.66 | 0.52 |
| GRAND MEAN | 33.367 | 33.111 | 10.450 | 13.811 | 4.94 | 6.17 | 5.00 | 6.56 |
| MIN. MEAN | 27.100 | 29.367 | 8.900 | 11.633 | 4.33 | 5.33 | 4.00 | 5.00 |
| MAX. MEAN | 34.867 | 38.533 | 13.467 | 19.700 | 5.33 | 7.67 | 5.67 | 9.00 |

TABLE 5D

| CULTIVAR | Lemma Length (mm) 2015 | 2016 | Lemma Width (mm) 2015 | 2016 | Lemma Awn Length (mm) 2016 | Glume Length (mm) 2015 | 2016 | Length of Spike (cm) 2015 | 2016 |
|---|---|---|---|---|---|---|---|---|---|
| AMFT114 | 7.700 | 7.533 | 1.667 | 1.433 | 0.200 | 5.100 | 4.933 | 23.600 | 22.167 |
| APRT2344 | 7.333 | 7.133 | 1.500 | 1.233 | 0.000 | 9.933 | 9.900 | 21.067 | 20.533 |
| APMT002 | 7.933 | 7.367 | 1.833 | 1.467 | 0.233 | 10.433 | 10.133 | 26.433 | 26.033 |
| APMT003 | 7.667 | 7.433 | 1.733 | 1.433 | 0.033 | 10.600 | 10.333 | 24.300 | 23.033 |
| APMT004 | 8.100 | 7.700 | 1.767 | 1.433 | 0.067 | 10.367 | 9.867 | 25.100 | 23.800 |
| APMT005 | 7.833 | 7.767 | 1.800 | 1.433 | 0.000 | 10.933 | 10.967 | 24.733 | 24.200 |
| CV | 3.274 | 2.482 | 8.705 | 3.597 | 157.321 | 4.130 | 4.310 | 5.774 | 6.491 |
| LSD (0.05) | 0.376 | 0.275 | 0.221 | 0.075 | 0.207 | 0.584 | 0.597 | 2.068 | 2.238 |
| GRAND MEAN | 7.761 | 7.489 | 1.717 | 1.406 | 0.089 | 9.561 | 9.356 | 24.206 | 23.294 |
| MIN. MEAN | 7.333 | 7.133 | 1.500 | 1.233 | 0.000 | 5.100 | 4.933 | 21.067 | 20.533 |
| MAX. MEAN | 8.100 | 7.767 | 1.833 | 1.467 | 0.233 | 10.933 | 10.967 | 26.433 | 26.033 |

TABLE 5E

| CULTIVAR | Spikelets Per Spike Count 2015 | 2016 | Florets Per Spikelet Count 2015 | 2016 | Spikelet Length (mm) 2015 | 2016 |
|---|---|---|---|---|---|---|
| AMFT114 | 53.00 | 48.33 | 6.67 | 7.00 | 16.600 | 16.833 |
| APRT2344 | 21.67 | 20.33 | 7.67 | 7.67 | 14.333 | 14.433 |
| APMT002 | 27.33 | 25.67 | 8.00 | 8.00 | 16.333 | 16.133 |
| APMT003 | 25.33 | 24.00 | 7.67 | 8.00 | 15.533 | 15.467 |

TABLE 5E-continued

| CULTIVAR | Spikelets Per Spike Count | | Florets Per Spikelet Count | | Spikelet Length (mm) | |
|---|---|---|---|---|---|---|
| | 2015 | 2016 | 2015 | 2016 | 2015 | 2016 |
| APMT004 | 27.67 | 25.67 | 8.33 | 9.00 | 16.833 | 17.033 |
| APMT005 | 26.33 | 25.00 | 8.67 | 8.33 | 16.233 | 16.600 |
| CV | 12.55 | 6.32 | 8.40 | 7.91 | 4.154 | 5.703 |
| LSD (0.05) | 5.61 | 2.63 | 0.97 | 0.94 | 0.982 | 1.357 |
| GRAND MEAN | 30.22 | 28.17 | 7.83 | 8.00 | 15.978 | 16.083 |
| MIN. MEAN | 21.67 | 20.33 | 6.67 | 7.00 | 14.333 | 14.433 |
| MAX. MEAN | 53.00 | 48.33 | 8.67 | 9.00 | 16.833 | 17.033 |

EXAMPLES

The following examples are furnished to further illustrate the present invention and are not intended to limit the invention beyond the examples set forth in the appended claim.

Example 1—Development of American Ryegrass (Turf Type *Festulolium*): Tetraploid Perennial Ryegrass Parent In 1990, the breeding research program that resulted in the tetraploid perennial ryegrass parent was initiated. The following breeding history describes the procedures used:

From 1990-2004, turf type perennial ryegrass populations were developed through traditional plant breeding methodologies for open-pollinated species. One of the resulting populations was APR1797. APR1797 is comprised of 13 lines sprigged from the 03LLP2 turf trial in New Jersey. The plants selected for resistance to gray leaf spot. Gray leaf spot disease is caused by the fungus Pyricularia *grisea*, also referred to as *Magnaporthe grisea*. 150 plants from each line were planted, the lines interpollinated and harvested by progeny line and designated APR1797.

In Fall 2004, seed of APR1797 was sent to a laboratory for chromosome doubling, as follows:

2004 Day 1

1. 1.5 grams of seed from each experimental line is weighed and replicated eight times.
2. A check for each line is also weighed.
3. The seeds are disinfected for 30 minutes in a 2% thiram solution.
4. The seeds are then washed for two hours in a running water bath at 35 degree Celsius.
5. The seeds are placed on blotting paper and dried for three hours at 35 degree Celsius.
6. The seeds are then wrapped in a wet blotting paper for germination. The seeds are placed in a controlled environment; 21 degree Celsius for 24 hours.

2004 Day 3

1. The seeds are inspected for root length. The root length for optimal colchicine treatment is 2-3 mm. All the seeds with root length of 2-3 mm are placed in a petri dish. The seeds are kept separate by experimental line, as are the checks.
2. Colchicine solution: 0.2 grams colchicine, 1 ml Tween 80, 1 ml DMSO, 98 ml distilled water.
3. Add 3 ml colchicine solution to each Petri dish; 3 ml of distilled water to the checks. Shake the Petri dishes gently for good distribution of the colchicine. Place the colchicine treated seeds in the dark for 2 hours at 30 degree Celsius.
4. The seeds are placed in a strainer and rinsed with water for 15 minutes.
5. The seeds are placed on blotting paper and placed in a germinator; 20 degree Celsius for 5-10 days.

2004 Day 8-12

1. The 4N plants can be removed from the other seedlings; the 4N plants are thicker.
2. For many of the seeds, the colchicine will be lethal; for some of the seeds the colchicine will not enter the tissue, resulting in normal 2N plants.
3. The 4N plants are planted in soil and moved to the greenhouse.

Fall 2004, plants moved into isolated crossing block in field.

Spring 2005, plants in the field are rechecked, by flow cytometry, to confirm all are still 4N. Any plants not 4N are removed from the nursery.

Summer 2005, plants harvested and seed was sent by to NexGen, Albany, Oreg. and designated APRT2066. In August, the seed was started and seedlings checked by flow cytometry for ploidy level. Any plant found to be not 4N was discarded.

In September 2005, a single spaced plant increase nursery was established. From seed. Plants used to start a plant selection field of 100 plants per block replicated 5 times.

May 2006, the nursery was evaluated for; dark genetic color, fine leaf texture, crown density, and freedom from disease (*Puccinia graminis*).

Summer 2006. After evaluation for plant type and ploidy, 264 clones were moved together for hybridization, and designated APRT2114; 27 clones were removed for being early in heading; the plants were confirmed to be 4N, with a flow cytometer, prior to flowering.

Summer 2007, seed of APRT2114 was harvested and bulked.

APRT2114 went through two cycles of selection for resistance to *Pypiculeria grisea* (Gray Leafspot) and was designated APRT2344.

This will be one of the parents of American ryegrass.

Tetraploid Meadow Fescue Parent:

In 1988, the breeding research program that resulted in the tetraploid meadow fescue parent was initiated. The following breeding history describes the procedures used:

From 1988-2010, turf type meadow fescue populations were developed through traditional plant breeding methodologies for open-pollinated species. One of the resulting populations was AMF112. AMF112 in comprised of the top 102 progeny (>68 g/plant) bulked of AMF109 from an 800 plant nursery.

In Summer 2010, seed of AMF112 was doubled in chromosome at the NexGen Turf Research facility in Albany, Oreg., as follows:

2010 Day 1

1. 1.5 grams of seed from each experimental line is weighed and replicated eight times.
2. A check for each line is also weighed.
3. The seeds are disinfected for 30 minutes in a 2% thiram solution.
4. The seeds are then washed for two hours in a running water bath at 35 degree Celsius.
5. The seeds are placed on blotting paper and dried for three hours at 35 degree Celsius.
6. The seeds are then wrapped in a wet blotting paper for germination. The seeds are placed in a controlled environment; 21 degree Celsius for 24 hours.

2010 Day 3

1. The seeds are inspected for root length. The root length for optimal colchicine treatment is 2-3 mm. All the seeds with root length of 2-3 mm are placed in a petri dish. The seeds are kept separate by experimental line, as are the checks.
2. Colchicine solution: 0.2 grams colchicine, 1 ml Tween 80, 1 ml DMSO, 98 ml distilled water.
3. Add 3 ml colchicine solution to each Petri dish; 3 ml of distilled water to the checks. Shake the Petri dishes gently for good distribution of the colchicine. Place the colchicine treated seeds in the dark for 2 hours at 30 degree Celsius.
4. The seeds are placed in a strainer and rinsed with water for 15 minutes.
5. The seeds are placed on blotting paper and placed in a germinator; 20 degree Celsius for 5-10 days.

2010 Day 8-12

1. The 4N plants can be removed from the other seedlings; the 4N plants are thicker.
2. For many of the seeds, the colchicine will be lethal. For some of the seeds the colchicine will not enter the tissue, resulting in normal 2N plants.
3. The 4N plants are planted in soil and moved to the greenhouse and designated AMFT114.

This is the second parent of American ryegrass.
Hybridization and Development of APMT001 Turf Type *Festulolium* (American Ryegrass)

Fall 2010: 76 were plants of AMFT114 were moved into isolated crossing block in field. Fifteen of these plants were used to cross with APRT2344.

2010: APMT001: 10 isolated single plant crosses were made crossing APRT2344 (female) x AMFT114 (male), 9 plants of APRT2344 were crossed by AMFT114. The cross was harvested by the female line APRT2344. The seed was bulked and designated APMT001. The first population of Turf Type *Festulolium* (American Ryegrass)

2011: A plant selection field (PSF) was established with APRT2344 and AMFT114 planted in borders to verify that APMT001 was a hybrid;

Table 6 provides the breeding history for the 11 populations of Turf Type *Festulolium* (American Ryegrass).

TABLE 6

| | | | Breeding Code | General Comments | Description of Process |
|---|---|---|---|---|---|
| A75 | 2 | *Festulolium* | APMT001 | A7501 - APRT2344 x AMFT114 | APMT001: 10 isolated single plant crosses were made crossing APRT2344 (female) x AMFT114 (male), 9 plants of APRT2344 were crossed by AMFT114. The cross was harvested by the female line APRT2344. The seed was bulked and designated APMT001.<br>2011: PSF was established with APRT2344 and AMFT114 planted in borders to verify that APMT001 was a hybrid; |
| A75 | 2 | *Festulolium* | APMT002 | A7501 - APMT001 | APMT002: 40 winter active clones were moved together prior to anthesis, criteria = winter active & not similar in appearance to the perennial ryegrass (4X) border,<br>2012: removed 8 clones at harvest due to poor fertility and seed set;<br>2013: Trialed in 13LFP1. 13AFP1;<br>2015: 14PVPFL1; |
| A75 | 2 | *Festulolium* | APMT003 | A7501 - fine leaf selection from APMT002 | APMT003: 50 winter active clones were moved together prior to anthesis, criteria = winter active, good crown density, fine leaf texture.<br>2013: moved clonal group together in the spring (4/13); Harvest by progeny; Endophyte seed survey = 100% (12/13); bulked 36 clones of >30 grams of seed; Trialed in 13LFP1. 13AFP1;<br>2014: 14AFA1, 14LFA1, 14RFA1, 14UFA1; 14PVPFL1.<br>2015: Trialed in 15LFL1, 15ALP2; |

TABLE 6-continued

| | | | Breeding Code | General Comments | Description of Process |
|---|---|---|---|---|---|
| A75 | 2 | Festulolium | APMT004 | A7501 - fescue type leaf selection from APMT002 | APMT004: 50 winter active clones were moved together prior to anthesis, criteria = winter active, good crown density, leaf texture similar to meadow fescue. 2013: moved clonal group together in the spring (4/20); Harvest by progeny; Endophyte seed survey = 100% (12/13); bulked 27 clones of >20 grams; 13LFP1; 13AFP1; 2014: Trialed in 14YLDLP1, 14AFA1, 14LFA1, 14RFA1, 14UFA1; 14PVPFL1; 2015: Trialed in 15ALP2; 15LFL1; |
| A75 | 1 | Festulolium | APMT005 | A7501 - selection from APMT003 | APMT005: selection from APMT003; 2013: 500 plant block of APMT003 planted on NARF. 2014: 38 plants selected from APMT003. Plants moved together in isolation before anthesis; Harvest in bulk; Trialed in 14YLDLP1; 14PVPFL1; 2015: Trialed in 15ALP2; 15LFL1; |
| A75 | 1 | Festulolium | APMT006 | A7501 - selection from APMT003 | APMT006: selection from APMT003; 2013: 500 plant block of APMT003 planted on NARF. 2014: 38 plants selected from APMT003 after summer stress; no irrigation applied summer 2014. 2015: Trialed in 15ALP2; 15LFL1; |
| A75 | 2 | Festulolium | APMT007 | A7501 - progeny yield selection from APMT004 | APMT007: 54 progeny were selected with yields greater than 90 grams per progeny. 2014: 2015: Trialed in 15ALP2; 15LFL1 + progeny; |
| A75 | 1 | Festulolium | APMT008 | A7501 - progeny yield selection from APMT005 | APMT008: 55 progeny were selected with yields greater than 100 grams per progeny. 2014: 2015: Trialed in 15ALP2; 15FL1 + progeny; |
| | | Festulolium | APMT009 | A7501 - surv. Removed from 15LFL1 from APMT006 | APMT009: 100 plants removed from 15LFL1. 2016: established MB. 2017: Harvest MB. |
| | | Festulolium | APMT010 | A7501 - surv. Removed from 15LFL1 top progeny from APMT007 | APMT010: Removed top progeny lines from 15LFL1. 2016: Removed 10 plants from the following progeny; 5, 7, 9, 11, 12, 13, 17, 21, 25, 31, 32, 33, 34, 43, 49, 51, 53. Established MB. 2017: Harvest MB. |
| | | Festulolium | APMT011 | A7501 - surv. Removed from 15LFL1 top progeny from APMT008 | APMT011: Removed top progeny lines from 15LFL1. 2016: Removed 10 plants from the following progeny; 1, 5, 7, 8, 12, 13, 17, 21, 22, 24, 25, 27, 30, 32, 36, 37, 38, 39, 40, 46, 47, 48, 53, 54, 55. Established MB. 2017: Harvest MB. |

Example 2—Comparison with Other Turfgrasses

American ryegrass is the first *Festulolium* turf type to be used for turf application. American ryegrass is also the first *Festulolium* turf type that exhibits a fine leaf texture and dark leaf color. Leaf color is the density of chlorophyll in the leaf blade, resulting in the intensity of color. In the turfgrass industry, dark green color is preferred. The dark green color gives an impression of a more healthy vigorous turf.

Turf color can be measured quantitatively and qualitatively. Qualitatively, the relative color of the different cultivars can be scored using a 1-9 visual scale, 9 being the darkest green. Digital analysis can also be used to determine color. A digital picture is taken of the turf. The software program Sigma Scan is used to convert the pixel image to a standard color wheel (hue, saturation and brightness). It then generates a number on a 1-9 scale, with 9 being the darkest green.

Table 7, illustrates the visual comparisons for several cultivars taken in Albany, Oreg. during 2016. The ratings are based on the following: 1=light green; 3=medium-light green; 5=medium green; 7=medium-dark green; 9=dark green.

TABLE 7

| Program | Cultivar | Winter Cover Ave. 2016 | Winter Density Ave. 2016 | Winter Genetic Ave. Color 2016 | Winter Turf Quality Ave. 2016 | Cover Ave. 2016 | Density Ave. 2016 | Genetic Color Ave. 2016 | Turf Quality Ave. 2016 |
|---|---|---|---|---|---|---|---|---|---|
| PSC | Soprano | 7.33 | 6.42 | 6.75 | 7.00 | 8.06 | 5.72 | 7.78 | 7.61 |
| TMI | Manhattan 6 | 7.33 | 6.08 | 6.33 | 6.58 | 7.83 | 5.83 | 7.56 | 7.56 |
| TMI | Pizzazz 2 | 7.67 | 6.25 | 6.17 | 6.75 | 8.06 | 5.33 | 7.05 | 7.05 |
| A7705 | AMFT118 | 4.92 | 4.25 | 6.25 | 4.50 | 7.50 | 6.16 | 6.33 | 6.95 |
| ProSeeds | APRT2114 | 6.83 | 5.08 | 6.75 | 6.00 | 7.72 | 5.11 | 7.17 | 6.78 |
| A7704 | AMF117 | 6.08 | 5.08 | 5.42 | 5.08 | 7.67 | 6.50 | 5.56 | 6.72 |
| Check | Pop | 7.00 | 5.75 | 6.00 | 5.92 | 7.44 | 4.61 | 7.33 | 6.56 |
| A7501 | APMT005 | 6.67 | 5.00 | 6.75 | 5.92 | 6.56 | 6.06 | 6.56 | 6.33 |
| A7501 | APMT006 | 6.42 | 5.08 | 6.33 | 5.67 | 6.83 | 6.17 | 5.83 | 6.33 |
| A7501 | APMT003 | 6.67 | 5.17 | 6.50 | 6.00 | 6.33 | 6.39 | 6.11 | 6.28 |
| A7501 | APMT004 | 6.92 | 5.50 | 6.17 | 5.83 | 5.78 | 7.22 | 5.44 | 6.05 |
| A7501 | APMT008 | 6.17 | 4.92 | 6.58 | 5.50 | 6.89 | 4.94 | 6.22 | 5.72 |
| A7350 | APR2936 | 7.17 | 5.17 | 5.08 | 5.42 | 7.11 | 4.89 | 5.72 | 5.67 |
| A7350 | APR2931 | 7.00 | 5.42 | 5.33 | 5.50 | 7.06 | 5.28 | 5.33 | 5.61 |
| A7350 | APR2916 | 5.83 | 4.67 | 4.42 | 4.08 | 6.94 | 4.67 | 5.83 | 5.44 |
| A7501 | APMT007 | 6.83 | 5.25 | 6.08 | 5.75 | 6.00 | 6.22 | 5.33 | 5.44 |
|  | CV | 4.61 | 7.48 | 5.29 | 6.34 | 2.70 | 6.76 | 3.17 | 4.45 |
|  | LSD (0.05) | 0.42 | 0.57 | 0.39 | 0.48 | 0.27 | 0.50 | 0.27 | 0.38 |

2016 Average Winter Cover = 1-9;
9 = Most Cover (2 ratings)
2016 Average Winter Genetic Color = 1-9;
9 = Darkest (2 ratings)
2016 Average Winter Density = 1-9;
9 = Most Dense (2 ratings)
2016 Average Winter Turf Quality = 1-9;
9 = Best (2 ratings)
2016 Average Cover = 1-9;
9 = Most Cover (3 ratings)
2016 Average Genetic Color = 1-9;
9 = Darkest (3 ratings)
2016 Average Density = 1-9;
9 = Most Dense (3 ratings)
2016 Average Turf Quality = 1-9;
9 = Best (3 ratings)

Example 3—Overseeding Study

Materials and Methods:

This study was conducted during the 2015-2016 growing season for cool-season grasses in the transition zone under athletic field/fairway conditions. Forty-six entries of cool-season grasses (ryegrasses) listed in Table 1 were overseeded on a 'Patriot' bermudagrass (*Cynodon dactylon*) grown on Cecil sandy loam (fine kaolinitic, thermic, Typic Kanhapludults) on 15 Oct. 2015. Bermudagrass check plots, which were not overseeded, were included in the study for comparison. The field study was conducted at the North Carolina State University's Lake Wheeler Turfgrass Field Lab.

The overseeding study was conducted on Patriot bermudagrass that was scalped to 0.5 inch with a reel mower before overseeding. A shaker bottle was used to hand seed all plots accurately and uniformly. Ryegrass (*Lolium* spp.) entries were seeded at a rate of 12 pounds per 1000 ft2. Light irrigation was applied twice daily for three weeks following seeding. This was then reduced to a maximum of once per day to replace water loss from evapotranspiration.

The study was mown with a reel mower for the first time fifteen days after seeding at a 0.9-inch bench height and was mown at this height twice weekly until day 55. The mowing height was reduced to 0.75 inch on day 56 and was continued at this height until the end of the study. The study area was generally mown three times a week.

An application of 1 pound N per 1000 ft2 was applied using 24-0-11 on 11 November, followed by 0.5 pounds of N per 1000 ft2 from 24-0-11 on 2 December, 15 January, 19 February, 22 March, and 20 April. So, a total of 3.5 pounds of N per 1000 ft2 was applied during the study.

No herbicide, fungicide, or insecticides were applied to the area during the study.

Ratings included visual estimates of percent cover (0-100%), color (1=brown; 2=brownish-yellow; 3=yellow; 4=yellow-green; 5=greenish-yellow; 6=green; 7=bluish-green; 8=dark green; and 9=deep dark green), and quality (overall appearance and stand uniformity value) with 1=dead grass, 6=minimally acceptable, and 9=highest quality. Digital color photo analysis was conducted once monthly from day 28 through the end of the study. Photographs were taken using a Nikon D80 SLR camera and analyzed with ImageJ software to determine hue (H) saturation (S) and brightness (B) values. Digital green color index (DGCI) values were calculated (DGCI value=[(H−60)/60+(1−S)+(1−B)]/3). Red-Green-Blue (RGB) via digital image analysis was used to determine ryegrass genetic color. A visual 1-9 texture estimate was taken in March (168 DAP) with 1=very coarse and 9=fine. A visual 1-9 density estimate was taken in March (168 DAP) with 9 equaling maximum density. In addition to that data, in March (168 DAP) root shear ratings (N m force) were measured using a Clegg Shear tester.

The study was planted in a randomized complete block design with four replications. All data were subjected to analysis of variance. Means were separated using a Fisher's protected LSD test at 5% level of probability. Data were summarized as growth rate and color across date intervals and presented as gross means in Tables 10 and 14. Data collected from individual dates were summarized in tables and presented with LSD values and variation as CV %.

TABLE 8

Composition and seed source of cool-season turfgrasses evaluated in overseeding trials during the 2015-2016 winter season and transition period

| Entry Number | Entry Name | Seed Type | Sponsoring Company |
| --- | --- | --- | --- |
| 1 | SPR Overseeding Blend | Perennial | Ledeboer Seed LLC |
| 2 | Natural Knit | Perennial | Ledeboer Seed LLC |
| 3 | Divine | Perennial | Thomas Ag Service |
| 4 | Approach | Annual | Thomas Ag Service |
| 5 | Cascadia | Perennial | Thomas Ag Service |
| 6 | Turf Merchant 50/50 Mix | Perennial/Intermediate | Turf Merchants |
| 7 | Turf Merchant 75/25 Mix | Perennial/Intermediate | Turf Merchants |
| 8 | Allaire 3 | Perennial | Turf Merchants |
| 9 | Nomad 4 | Perennial | Turf Merchants |
| 10 | Palmetto | Intermediate | Turf Merchants |
| 11 | CS-IR-228 | Not Specified | Columbia Seeds |
| 12 | CS-AT-1 | Not Specified | Columbia Seeds |
| 13 | CS-AR-106 | Not Specified | Columbia Seeds |
| 14 | CS-CO-1 | Not Specified | Columbia Seeds |
| 15 | CS-PRB | Not Specified | Columbia Seeds |
| 16 | APMT005 | Not Specified | Nexgen Turf Research |
| 17 | Seabiscuit | Perennial | Lebanon Seaboard Corp. |
| 18 | Man O'War | Perennial | Lebanon Seaboard Corp. |
| 19 | HS-35 | Perennial | Allied Seed |
| 20 | HS-36 | Perennial | Allied Seed |
| 21 | ASP1001 GL | Perennial | Allied Seed |
| 22 | ASP0112 | Perennial | Allied Seed |
| 23 | ASP0113 | Perennial | Allied Seed |
| 24 | ASP6002 | Perennial | Allied Seed |
| 25 | Frontier | Perennial | Allied Seed |
| 26 | Singular | Perennial | Allied Seed |
| 27 | Solstice II | Intermediate | Mountain View Seeds |
| 28 | Breakout | Annual | Mountain View Seeds |
| 29 | PPG-PR-321 | Perennial | Mountain View Seeds |
| 30 | PPG-PR-303 | Perennial | Mountain View Seeds |
| 31 | PPG-PR-308 | Perennial | Mountain View Seeds |
| 32 | Replicator | Perennial | DLF Pickseed USA |
| 33 | Quickston | Annual | DLF Pickseed USA |
| 34 | PSAR-09-2 | Annual | DLF Pickseed USA |
| 35 | Candidame | Annual | DLF Pickseed USA |
| 36 | Tetradark | Perennial | DLF Pickseed USA |
| 37 | FLIRFC-4 | Intermediate | DLF Pickseed USA |
| 38 | NAI-ALS5 | Perennial | Novel AG, Inc. |
| 39 | NAI-PL2 | Perennial | Novel AG, Inc. |
| 40 | NAI-LCP-186 | Perennial | Novel AG, Inc. |
| 41 | NAI-COM-ST | Perennial | Novel AG, Inc. |
| 42 | Prosport 4 | Perennial | Novel AG, Inc. |
| 43 | PPG-PR-172 | Perennial | Smith Seed Services |
| 44 | PPG-TAR-113 | Not Specified | Smith Seed Services |
| 45 | Gulf | Annual | Check entry, locally sourced |
| 46 | Carly | Perennial | Locally sourced |
| 47 | Untreated Control | NA | NA |

TABLE 9

| To determine month that data was taken, refer to key at bottom of table | | | | | | | | |
|---|---|---|---|---|---|---|---|---|
| First Day of Each Month | November | December | January | February | March | April | May | June |
| Days After Over-seeding | 17 | 47 | 78 | 109 | 138 | 169 | 199 | 230 |

TABLE 10

Overseed cover rate (%) estimates and (normalized) average daily coverage rate (%) for first 28 days after overseeding Patriot bermudagrass on 15 October

| Turfgrass | Cover Rate | Average daily coverage rate for first month |
|---|---|---|
| 1 | 3.14 | 3.15 |
| 2 | 2.93 | 2.92 |
| 3 | 3.07 | 2.98 |
| 4 | 3.17 | 3.04 |
| 5 | 3.14 | 3.10 |
| 6 | 3.17 | 2.98 |
| 7 | 3.14 | 3.10 |
| 8 | 3.38 | 3.21 |
| 9 | 2.95 | 2.92 |
| 10 | 2.88 | 2.92 |
| 11 | 3.10 | 2.92 |
| 12 | 2.90 | 2.80 |
| 13 | 2.76 | 2.74 |
| 14 | 3.05 | 2.86 |
| 15 | 2.95 | 2.74 |
| 16 | 2.48 | 2.50 |
| 17 | 3.14 | 3.10 |
| 18 | 2.95 | 2.92 |
| 19 | 3.31 | 3.21 |
| 20 | 3.26 | 3.15 |
| 21 | 2.98 | 2.98 |
| 22 | 3.07 | 3.04 |
| 23 | 2.88 | 2.74 |
| 24 | 2.86 | 2.80 |
| 25 | 2.86 | 2.86 |
| 26 | 3.02 | 2.92 |
| 27 | 3.17 | 2.92 |
| 28 | 3.21 | 3.10 |
| 29 | 2.69 | 2.68 |
| 30 | 3.00 | 3.04 |
| 31 | 2.57 | 2.68 |
| 32 | 2.74 | 2.62 |
| 33 | 3.19 | 2.98 |
| 34 | 3.50 | 3.21 |
| 35 | 3.02 | 2.92 |
| 36 | 2.33 | 2.50 |
| 37 | 2.93 | 2.92 |
| 38 | 3.29 | 3.10 |
| 39 | 2.50 | 2.62 |
| 40 | 3.21 | 3.10 |
| 41 | 3.14 | 2.98 |
| 42 | 3.02 | 2.98 |
| 43 | 2.93 | 2.86 |
| 44 | 2.86 | 2.80 |
| 45 | 3.48 | 3.15 |
| 46 | 3.45 | 3.21 |
| 47 | 0.00 | 0.00 |
| LSD (P = 0.05) | 0.343 | 0.321 |
| CV % | 7 | 7 |

TABLE 11

Cover rate estimates after overseeding Patriot bermudagrass on 15 October

| Turfgrass | Turfgrass Cover Estimates at Day | | | | | | | | | |
|---|---|---|---|---|---|---|---|---|---|---|
| | 7 | 14 | 21 | 28 | 42 | 56 | 70 | 84 | 98 | 112 |
| 1 | 3.33 | 48.33 | 80.00 | 88.33 | 91.67 | 91.67 | 96.67 | 98.33 | 98.33 | 98.33 |
| 2 | 5.00 | 46.67 | 71.67 | 81.67 | 86.67 | 90.00 | 93.33 | 95.00 | 95.00 | 95.00 |
| 3 | 1.67 | 53.33 | 76.67 | 83.33 | 88.33 | 91.67 | 95.00 | 96.67 | 96.67 | 96.67 |
| 4 | 3.33 | 58.33 | 75.00 | 85.00 | 86.67 | 91.67 | 95.00 | 96.67 | 95.67 | 95.67 |
| 5 | 5.00 | 50.00 | 78.33 | 86.67 | 91.67 | 95.00 | 96.67 | 98.33 | 98.33 | 98.33 |
| 6 | 3.33 | 56.67 | 78.33 | 83.33 | 83.33 | 91.67 | 91.67 | 96.67 | 95.67 | 95.67 |
| 7 | 5.00 | 51.67 | 76.67 | 86.67 | 90.00 | 91.67 | 96.67 | 98.33 | 96.33 | 96.33 |
| 8 | 5.00 | 60.00 | 81.67 | 90.00 | 93.33 | 95.00 | 98.33 | 98.33 | 98.33 | 98.33 |
| 9 | 5.00 | 46.67 | 73.33 | 81.67 | 85.00 | 88.33 | 93.33 | 97.33 | 97.33 | 97.33 |
| 10 | 1.67 | 46.67 | 71.67 | 81.67 | 85.00 | 90.00 | 93.33 | 95.00 | 94.00 | 94.00 |
| 11 | 1.67 | 55.00 | 78.33 | 81.67 | 83.33 | 88.33 | 91.67 | 95.00 | 95.00 | 95.00 |
| 12 | 1.67 | 51.67 | 71.67 | 78.33 | 83.33 | 88.33 | 90.00 | 96.67 | 96.67 | 96.67 |
| 13 | 0.00 | 48.33 | 68.33 | 76.67 | 80.00 | 86.67 | 88.33 | 93.33 | 93.33 | 93.33 |
| 14 | 5.00 | 55.00 | 73.33 | 80.00 | 80.00 | 83.33 | 85.00 | 90.00 | 90.00 | 90.00 |
| 15 | 5.00 | 51.67 | 73.33 | 76.67 | 81.67 | 86.67 | 88.33 | 88.33 | 88.33 | 88.33 |
| 16 | 5.00 | 36.67 | 61.67 | 70.00 | 71.67 | 78.33 | 80.00 | 83.33 | 83.33 | 83.33 |
| 17 | 5.00 | 50.00 | 78.33 | 86.67 | 86.67 | 91.67 | 93.33 | 96.67 | 96.67 | 96.67 |
| 18 | 3.33 | 50.00 | 71.67 | 81.67 | 85.00 | 90.00 | 91.67 | 96.67 | 96.67 | 96.67 |
| 19 | 5.00 | 56.67 | 80.00 | 90.00 | 91.67 | 96.67 | 96.67 | 98.33 | 98.33 | 98.33 |
| 20 | 3.33 | 56.67 | 80.00 | 88.33 | 90.00 | 95.00 | 95.00 | 96.67 | 96.67 | 96.67 |
| 21 | 0.00 | 48.33 | 76.67 | 83.33 | 90.00 | 93.33 | 93.33 | 95.00 | 95.00 | 95.00 |
| 22 | 3.33 | 50.00 | 76.67 | 85.00 | 86.67 | 90.00 | 93.33 | 95.00 | 93.33 | 93.33 |
| 23 | 3.33 | 50.00 | 71.67 | 76.67 | 81.67 | 86.67 | 88.33 | 95.00 | 95.00 | 95.00 |
| 24 | 5.00 | 45.00 | 71.67 | 78.33 | 83.33 | 86.67 | 90.00 | 93.33 | 93.33 | 93.33 |
| 25 | 5.00 | 43.33 | 71.67 | 80.00 | 85.00 | 88.33 | 91.67 | 96.67 | 96.67 | 95.00 |
| 26 | 3.33 | 51.67 | 75.00 | 81.67 | 86.67 | 91.67 | 91.67 | 96.67 | 96.67 | 96.67 |

TABLE 11-continued

Cover rate estimates after overseeding Patriot bermudagrass on 15 October

| Turfgrass | \multicolumn{10}{c}{Turfgrass Cover Estimates at Day} | | | | | | | | | |
|---|---|---|---|---|---|---|---|---|---|---|
| | 7 | 14 | 21 | 28 | 42 | 56 | 70 | 84 | 98 | 112 |
| 27 | 1.67 | 60.00 | 78.33 | 81.67 | 85.00 | 88.33 | 93.33 | 93.33 | 88.33 | 88.33 |
| 28 | 1.67 | 56.67 | 80.00 | 86.67 | 88.33 | 95.00 | 98.33 | 100.00 | 98.33 | 98.33 |
| 29 | 3.33 | 41.67 | 68.33 | 75.00 | 81.67 | 85.00 | 88.33 | 93.33 | 93.33 | 93.33 |
| 30 | 1.67 | 46.67 | 76.67 | 85.00 | 90.00 | 95.00 | 95.00 | 97.33 | 97.33 | 97.33 |
| 31 | 3.33 | 35.00 | 66.67 | 75.00 | 80.00 | 85.00 | 88.33 | 91.67 | 91.67 | 91.67 |
| 32 | 3.33 | 46.67 | 68.33 | 73.33 | 76.67 | 80.00 | 83.33 | 88.33 | 88.33 | 88.33 |
| 33 | 5.00 | 58.33 | 76.67 | 83.33 | 85.00 | 90.00 | 93.33 | 96.67 | 93.33 | 93.33 |
| 34 | 3.33 | 68.33 | 83.33 | 90.00 | 90.00 | 93.33 | 95.00 | 96.67 | 95.00 | 95.00 |
| 35 | 1.67 | 53.33 | 75.00 | 81.67 | 83.33 | 90.00 | 93.33 | 98.33 | 98.33 | 98.33 |
| 36 | 1.67 | 33.33 | 58.33 | 70.00 | 73.33 | 80.00 | 83.33 | 90.00 | 90.00 | 90.00 |
| 37 | 1.67 | 48.33 | 73.33 | 81.67 | 85.00 | 91.67 | 95.00 | 96.67 | 96.67 | 96.67 |
| 38 | 5.00 | 58.33 | 80.00 | 86.67 | 88.33 | 91.67 | 95.00 | 98.33 | 98.33 | 98.33 |
| 39 | 5.00 | 35.00 | 61.67 | 73.33 | 78.33 | 85.00 | 88.33 | 93.33 | 93.33 | 93.33 |
| 40 | 5.00 | 55.00 | 78.33 | 86.67 | 88.33 | 91.67 | 91.67 | 96.67 | 96.67 | 96.67 |
| 41 | 3.33 | 56.67 | 76.67 | 83.33 | 88.33 | 91.67 | 93.33 | 96.67 | 96.67 | 96.67 |
| 42 | 3.33 | 50.00 | 75.00 | 83.33 | 85.00 | 88.33 | 90.00 | 95.00 | 95.00 | 95.00 |
| 43 | 0.00 | 51.67 | 73.33 | 80.00 | 85.00 | 88.33 | 91.67 | 95.00 | 95.00 | 95.00 |
| 44 | 1.67 | 48.33 | 71.67 | 78.33 | 86.67 | 93.33 | 95.00 | 96.67 | 95.00 | 95.00 |
| 45 | 5.00 | 66.67 | 83.33 | 88.33 | 88.33 | 93.33 | 93.33 | 95.00 | 91.67 | 90.00 |
| 46 | 5.00 | 63.33 | 83.33 | 90.00 | 91.67 | 93.33 | 96.67 | 98.33 | 98.33 | 98.33 |
| 47 | 0.00 | 0.00 | 0.00 | 0.00 | 0.00 | 0.00 | 0.00 | 0.00 | 0.00 | 0.00 |
| LSD (P = 0.05) | 3.3 | 8.5 | 9.1 | 8.9 | 8.4 | 8.7 | 8.4 | 6.9 | 6.8 | 6.9 |
| CV % | 64 | 11 | 8 | 7 | 6 | 6 | 6 | 5 | 5 | 5 |

TABLE 12

Cover rate estimates after overseeding Patriot bermudagrass on 15 October

| Turfgrass | \multicolumn{9}{c}{Turfgrass Cover Estimates at Day} | | | | | | | | |
|---|---|---|---|---|---|---|---|---|---|
| | 126 | 140 | 154 | 168 | 182 | 196 | 210 | 224 | 238 |
| 1 | 98.33 | 98.33 | 100.00 | 100.00 | 100.00 | 100.00 | 91.67 | 58.33 | 48.33 |
| 2 | 95.00 | 95.00 | 98.33 | 98.33 | 98.33 | 98.33 | 83.33 | 55.00 | 41.67 |
| 3 | 96.67 | 96.67 | 96.67 | 98.33 | 98.33 | 98.33 | 85.00 | 53.33 | 40.00 |
| 4 | 95.67 | 98.33 | 98.33 | 98.33 | 98.33 | 98.33 | 75.00 | 40.00 | 8.33 |
| 5 | 98.33 | 100.00 | 100.00 | 100.00 | 100.00 | 100.00 | 81.67 | 41.67 | 36.67 |
| 6 | 95.67 | 96.67 | 100.00 | 100.00 | 100.00 | 100.00 | 83.33 | 36.67 | 15.00 |
| 7 | 96.33 | 98.33 | 98.33 | 98.33 | 98.33 | 100.00 | 83.33 | 41.67 | 26.67 |
| 8 | 98.33 | 98.33 | 98.33 | 100.00 | 100.00 | 100.00 | 83.33 | 48.33 | 40.00 |
| 9 | 97.33 | 99.00 | 100.00 | 100.00 | 100.00 | 100.00 | 90.00 | 51.67 | 38.33 |
| 10 | 94.00 | 95.67 | 96.67 | 98.33 | 98.33 | 100.00 | 83.33 | 40.00 | 21.67 |
| 11 | 95.00 | 95.00 | 96.67 | 100.00 | 100.00 | 100.00 | 80.00 | 43.33 | 20.00 |
| 12 | 96.67 | 96.67 | 96.67 | 98.33 | 98.33 | 100.00 | 78.33 | 28.33 | 21.67 |
| 13 | 93.33 | 95.67 | 96.67 | 98.33 | 98.33 | 100.00 | 78.33 | 28.33 | 6.67 |
| 14 | 90.00 | 90.00 | 93.33 | 95.00 | 95.00 | 95.00 | 78.33 | 33.33 | 26.67 |
| 15 | 88.33 | 88.33 | 93.33 | 95.00 | 95.00 | 96.67 | 83.33 | 33.33 | 15.00 |
| 16 | 81.67 | 83.33 | 90.00 | 93.33 | 93.33 | 93.33 | 75.00 | 26.67 | 8.33 |
| 17 | 96.67 | 96.67 | 98.33 | 98.33 | 98.33 | 98.33 | 81.67 | 40.00 | 35.00 |
| 18 | 95.00 | 96.67 | 100.00 | 100.00 | 100.00 | 100.00 | 85.00 | 46.67 | 33.33 |
| 19 | 98.33 | 98.33 | 100.00 | 100.00 | 100.00 | 100.00 | 90.00 | 51.67 | 48.33 |
| 20 | 96.67 | 96.67 | 96.67 | 98.33 | 98.33 | 98.33 | 81.67 | 38.33 | 30.00 |
| 21 | 95.00 | 95.00 | 95.00 | 96.67 | 96.67 | 96.67 | 86.67 | 48.33 | 35.00 |
| 22 | 93.33 | 93.33 | 93.33 | 93.33 | 95.00 | 96.67 | 81.67 | 51.67 | 30.00 |
| 23 | 95.00 | 95.00 | 98.33 | 98.33 | 98.33 | 98.33 | 88.33 | 38.33 | 21.67 |
| 24 | 93.33 | 93.33 | 95.00 | 95.00 | 95.00 | 95.00 | 80.00 | 31.67 | 21.67 |
| 25 | 95.00 | 96.67 | 98.33 | 100.00 | 100.00 | 100.00 | 88.33 | 50.00 | 33.33 |
| 26 | 96.67 | 96.67 | 98.33 | 98.33 | 98.33 | 98.33 | 81.67 | 43.33 | 33.33 |
| 27 | 88.33 | 90.00 | 93.33 | 96.67 | 96.67 | 96.67 | 78.33 | 41.67 | 16.67 |
| 28 | 98.33 | 99.00 | 99.00 | 100.00 | 100.00 | 100.00 | 80.00 | 43.33 | 21.67 |
| 29 | 93.33 | 93.33 | 95.00 | 95.00 | 95.00 | 98.33 | 83.33 | 53.33 | 33.33 |
| 30 | 97.33 | 98.33 | 98.33 | 100.00 | 100.00 | 100.00 | 91.67 | 65.00 | 48.33 |
| 31 | 90.00 | 90.00 | 95.00 | 98.33 | 98.33 | 100.00 | 86.67 | 46.67 | 31.67 |
| 32 | 88.33 | 88.33 | 91.67 | 93.33 | 93.33 | 98.33 | 83.33 | 36.67 | 21.67 |
| 33 | 93.33 | 93.33 | 96.67 | 96.67 | 96.67 | 98.33 | 76.67 | 40.00 | 11.67 |
| 34 | 93.33 | 93.33 | 98.33 | 100.00 | 100.00 | 100.00 | 66.67 | 25.00 | 8.33 |
| 35 | 96.67 | 99.00 | 99.00 | 100.00 | 100.00 | 100.00 | 81.67 | 40.00 | 16.67 |
| 36 | 88.33 | 88.33 | 93.33 | 95.00 | 95.00 | 95.00 | 80.00 | 36.67 | 21.67 |
| 37 | 96.67 | 98.33 | 98.33 | 100.00 | 100.00 | 100.00 | 88.33 | 48.33 | 30.00 |
| 38 | 98.33 | 98.33 | 98.33 | 100.00 | 100.00 | 100.00 | 83.33 | 43.33 | 21.67 |

TABLE 12-continued

Cover rate estimates after overseeding Patriot bermudagrass on 15 October

| Turfgrass | \multicolumn{9}{c}{Turfgrass Cover Estimates at Day} |
|---|---|---|---|---|---|---|---|---|---|
| | 126 | 140 | 154 | 168 | 182 | 196 | 210 | 224 | 238 |
| 39 | 93.33 | 93.33 | 96.67 | 98.33 | 98.33 | 98.33 | 88.33 | 46.67 | 36.67 |
| 40 | 96.67 | 96.67 | 98.33 | 100.00 | 100.00 | 100.00 | 78.33 | 38.33 | 21.67 |
| 41 | 96.67 | 96.67 | 96.67 | 96.67 | 98.33 | 100.00 | 86.67 | 51.67 | 38.33 |
| 42 | 95.00 | 95.00 | 98.33 | 100.00 | 100.00 | 100.00 | 81.67 | 40.00 | 26.67 |
| 43 | 95.00 | 95.67 | 96.67 | 98.33 | 98.33 | 100.00 | 88.33 | 60.00 | 43.33 |
| 44 | 95.00 | 95.00 | 96.67 | 98.33 | 98.33 | 100.00 | 83.33 | 36.67 | 8.33 |
| 45 | 86.67 | 91.67 | 95.00 | 96.67 | 96.67 | 98.33 | 70.00 | 36.67 | 8.33 |
| 46 | 98.33 | 100.00 | 98.33 | 98.33 | 98.33 | 100.00 | 88.33 | 50.00 | 33.33 |
| 47 | 0.00 | 0.00 | 0.00 | 0.00 | 0.00 | 0.00 | 0.00 | 0.00 | 0.00 |
| LSD (P = 0.05) | 7.1 | 6.8 | 5.5 | 3.9 | 3.9 | 3.2 | 8.6 | 18.1 | 17.5 |
| CV % | 5 | 5 | 4 | 3 | 3 | 2 | 7 | 27 | 42 |

TABLE 13

Color estimates after overseeding Patriot bermudagrass on 15 October. Turf color based on a 1-9 scale, where 1 = dead grass, 2 = dull yellow-green, 3 = pale yellow green, 4 = yellow green, 5 = pale green, 6 = green, 7 = dark green, 8 = deep dark green, and 9 = black green

| Turfgrass | \multicolumn{8}{c}{Turfgrass Color Estimates at Day} |
|---|---|---|---|---|---|---|---|---|
| | 42 | 56 | 70 | 84 | 98 | 112 | 126 | 140 |
| 1 | 7.00 | 7.67 | 7.67 | 8.00 | 7.00 | 7.33 | 7.33 | 7.33 |
| 2 | 7.00 | 7.33 | 7.33 | 7.67 | 7.00 | 7.00 | 6.67 | 7.00 |
| 3 | 6.00 | 6.67 | 7.00 | 7.00 | 6.67 | 6.67 | 6.33 | 6.67 |
| 4 | 4.33 | 5.00 | 5.00 | 5.00 | 4.00 | 5.00 | 4.67 | 4.67 |
| 5 | 7.33 | 8.00 | 8.00 | 8.00 | 8.00 | 8.00 | 8.00 | 8.00 |
| 6 | 4.33 | 5.00 | 5.00 | 5.00 | 4.67 | 5.00 | 4.33 | 5.33 |
| 7 | 5.00 | 6.00 | 6.33 | 6.33 | 5.67 | 5.67 | 5.67 | 5.67 |
| 8 | 5.67 | 6.67 | 6.67 | 7.00 | 6.67 | 6.67 | 6.00 | 6.67 |
| 9 | 6.00 | 6.00 | 7.00 | 7.00 | 6.33 | 6.33 | 6.00 | 6.33 |
| 10 | 5.00 | 6.33 | 6.33 | 7.00 | 6.00 | 6.00 | 6.00 | 6.00 |
| 11 | 4.33 | 5.00 | 5.00 | 5.67 | 5.67 | 5.67 | 5.33 | 6.00 |
| 12 | 7.00 | 7.67 | 7.00 | 7.00 | 6.67 | 7.00 | 7.00 | 7.00 |
| 13 | 5.00 | 5.67 | 6.00 | 6.33 | 5.00 | 5.33 | 5.00 | 5.33 |
| 14 | 5.67 | 6.33 | 6.33 | 6.33 | 5.33 | 6.00 | 5.33 | 5.67 |
| 15 | 5.67 | 6.00 | 6.33 | 6.33 | 6.33 | 6.33 | 5.67 | 5.67 |
| 16 | 5.00 | 5.33 | 5.33 | 5.67 | 4.00 | 4.67 | 4.33 | 5.33 |
| 17 | 6.00 | 7.00 | 7.00 | 7.00 | 6.67 | 7.00 | 6.33 | 6.67 |
| 18 | 6.67 | 7.00 | 7.00 | 7.33 | 7.67 | 7.33 | 7.33 | 7.67 |
| 19 | 7.33 | 8.00 | 8.00 | 8.00 | 7.33 | 8.00 | 7.67 | 8.00 |
| 20 | 7.00 | 7.33 | 7.33 | 7.33 | 7.00 | 7.33 | 6.67 | 7.33 |
| 21 | 7.00 | 7.33 | 7.67 | 7.67 | 7.33 | 7.67 | 7.00 | 7.00 |
| 22 | 7.33 | 7.33 | 7.33 | 7.33 | 7.00 | 7.33 | 6.67 | 7.33 |
| 23 | 6.67 | 7.00 | 7.33 | 7.33 | 7.00 | 7.00 | 6.67 | 7.33 |
| 24 | 6.67 | 6.67 | 6.67 | 6.67 | 6.33 | 6.67 | 6.33 | 6.33 |
| 25 | 6.67 | 7.00 | 7.33 | 7.33 | 7.00 | 7.33 | 7.00 | 7.00 |
| 26 | 7.00 | 7.00 | 7.33 | 7.33 | 6.00 | 6.33 | 7.00 | 6.00 |
| 27 | 4.33 | 5.33 | 5.33 | 5.33 | 4.33 | 4.67 | 4.33 | 4.67 |
| 28 | 5.00 | 5.67 | 6.00 | 6.33 | 4.67 | 5.33 | 5.00 | 5.67 |
| 29 | 6.00 | 6.00 | 6.00 | 6.33 | 5.67 | 6.33 | 5.33 | 6.00 |
| 30 | 7.00 | 7.67 | 7.67 | 7.67 | 7.67 | 7.67 | 7.67 | 7.67 |
| 31 | 6.33 | 7.00 | 7.00 | 7.00 | 6.67 | 7.00 | 6.67 | 7.00 |
| 32 | 5.33 | 5.67 | 5.67 | 6.00 | 5.00 | 5.00 | 4.67 | 5.33 |
| 33 | 4.67 | 5.33 | 5.67 | 5.67 | 4.00 | 5.00 | 4.67 | 5.00 |
| 34 | 4.00 | 5.00 | 5.00 | 5.00 | 3.33 | 4.33 | 4.00 | 4.67 |
| 35 | 5.00 | 6.00 | 6.00 | 6.00 | 4.67 | 5.00 | 5.00 | 5.33 |
| 36 | 6.67 | 7.33 | 7.33 | 7.33 | 6.00 | 6.00 | 5.00 | 6.00 |
| 37 | 5.33 | 6.33 | 6.33 | 6.33 | 5.67 | 5.67 | 5.67 | 6.67 |
| 38 | 5.33 | 6.67 | 6.33 | 6.67 | 6.33 | 6.67 | 6.33 | 6.67 |
| 39 | 6.33 | 7.33 | 7.67 | 7.67 | 7.33 | 7.33 | 6.67 | 7.67 |
| 40 | 5.33 | 6.00 | 6.00 | 7.00 | 6.67 | 6.67 | 6.00 | 6.00 |
| 41 | 6.00 | 6.67 | 6.67 | 6.67 | 6.00 | 6.67 | 6.33 | 6.33 |
| 42 | 5.33 | 6.33 | 6.33 | 6.33 | 6.33 | 6.33 | 5.67 | 5.67 |
| 43 | 6.00 | 7.00 | 7.33 | 7.33 | 7.00 | 7.00 | 7.00 | 7.00 |
| 44 | 5.33 | 6.33 | 6.00 | 6.00 | 4.67 | 5.67 | 5.67 | 5.33 |
| 45 | 3.33 | 4.00 | 4.00 | 4.00 | 2.00 | 3.00 | 3.00 | 3.67 |
| 46 | 6.00 | 7.00 | 6.67 | 7.00 | 6.00 | 6.33 | 6.00 | 6.33 |
| 47 | 4.00 | 2.33 | 1.33 | 1.33 | 1.00 | 1.00 | 1.00 | 1.00 |
| LSD (P = 0.05) | 0.94 | 1.04 | 1.13 | 1.10 | 1.07 | 1.11 | 1.14 | 1.26 |
| CV % | 10 | 10 | 11 | 11 | 12 | 11 | 12 | 13 |

TABLE 14

Color estimates after overseeding Patriot bermudagrass on 15 October. Turf color based on a 1-9 scale, where 1 = dead grass, 2 = dull yellow-green, 3 = pale yellow green, 4 = yellow green, 5 = pale green, 6 = green, 7 = dark green, 8 = deep dark green, and 9 = black green. Note season mean estimate is influenced by early- and late-season bermudagrass color

| Turfgrass | \multicolumn{7}{c}{Turfgrass Color Estimates at Day} | Season Mean |
|---|---|---|---|---|---|---|---|---|
| | 154 | 168 | 182 | 196 | 210 | 224 | 238 | |
| 1 | 8.00 | 8.33 | 8.33 | 8.33 | 8.00 | 7.67 | 7.00 | 7.67 |
| 2 | 7.67 | 8.00 | 8.33 | 8.67 | 8.67 | 8.00 | 7.67 | 7.60 |
| 3 | 7.33 | 7.33 | 7.33 | 7.67 | 7.67 | 7.33 | 7.00 | 6.98 |
| 4 | 4.00 | 4.00 | 4.67 | 5.00 | 6.33 | 5.33 | 6.00 | 4.84 |
| 5 | 8.67 | 9.00 | 9.00 | 9.00 | 8.67 | 8.00 | 7.67 | 8.22 |
| 6 | 5.33 | 5.00 | 5.67 | 5.67 | 6.00 | 6.00 | 5.67 | 5.20 |
| 7 | 5.67 | 5.67 | 6.33 | 6.67 | 7.00 | 6.67 | 6.67 | 6.07 |
| 8 | 7.00 | 7.33 | 7.67 | 7.80 | 7.67 | 7.33 | 7.00 | 6.98 |
| 9 | 6.67 | 7.33 | 7.33 | 8.00 | 8.00 | 7.00 | 7.00 | 6.82 |
| 10 | 5.67 | 5.67 | 6.00 | 6.00 | 6.67 | 5.00 | 5.67 | 5.89 |
| 11 | 6.33 | 6.00 | 6.67 | 7.00 | 7.00 | 7.00 | 6.33 | 5.93 |
| 12 | 7.00 | 7.00 | 7.00 | 7.00 | 7.00 | 6.67 | 7.00 | 7.00 |
| 13 | 5.00 | 5.33 | 6.33 | 6.33 | 6.00 | 5.33 | 5.67 | 5.58 |
| 14 | 6.33 | 6.67 | 7.67 | 8.00 | 7.67 | 7.33 | 7.00 | 6.51 |
| 15 | 6.67 | 7.33 | 8.00 | 8.33 | 8.00 | 8.00 | 7.00 | 6.78 |
| 16 | 6.00 | 7.00 | 7.67 | 7.67 | 7.33 | 7.00 | 7.00 | 5.96 |
| 17 | 7.00 | 7.67 | 8.00 | 8.33 | 8.00 | 7.67 | 7.33 | 7.18 |
| 18 | 7.67 | 8.33 | 8.33 | 8.67 | 8.33 | 8.00 | 7.67 | 7.78 |
| 19 | 8.33 | 8.67 | 9.00 | 9.00 | 9.00 | 8.00 | 7.67 | 8.13 |
| 20 | 7.67 | 8.00 | 8.33 | 8.33 | 8.00 | 8.00 | 7.33 | 7.53 |
| 21 | 7.67 | 8.00 | 8.33 | 8.67 | 8.67 | 8.00 | 7.33 | 7.69 |
| 22 | 7.67 | 8.00 | 8.67 | 9.00 | 8.33 | 8.00 | 7.33 | 7.64 |
| 23 | 8.00 | 8.33 | 8.67 | 8.67 | 8.33 | 8.00 | 7.00 | 7.56 |
| 24 | 7.00 | 7.33 | 8.00 | 8.67 | 8.00 | 7.67 | 7.00 | 7.07 |
| 25 | 7.33 | 7.67 | 8.33 | 8.33 | 8.33 | 8.00 | 7.00 | 7.44 |

TABLE 14-continued

Color estimates after overseeding Patriot bermudagrass on 15 October. Turf color based on a 1-9 scale, where 1 = dead grass, 2 = dull yellow-green, 3 = pale yellow green, 4 = yellow green, 5 = pale green, 6 = green, 7 = dark green, 8 = deep dark green, and 9 = black green. Note season mean estimate is influenced by early- and late-season bermudagrass color

| Turfgrass | 154 | 168 | 182 | 196 | 210 | 224 | 238 | Season Mean |
|---|---|---|---|---|---|---|---|---|
| 26 | 7.67 | 7.67 | 8.67 | 9.00 | 8.67 | 8.00 | 7.00 | 7.42 |
| 27 | 4.33 | 4.67 | 5.33 | 5.67 | 5.67 | 5.00 | 5.33 | 4.96 |
| 28 | 5.67 | 5.67 | 5.67 | 6.00 | 5.67 | 4.33 | 5.00 | 5.44 |
| 29 | 6.67 | 7.00 | 7.67 | 8.33 | 8.33 | 8.00 | 7.00 | 6.71 |
| 30 | 8.67 | 8.67 | 8.67 | 8.67 | 8.33 | 8.00 | 7.33 | 7.93 |
| 31 | 7.33 | 7.67 | 8.67 | 9.00 | 8.67 | 8.00 | 7.00 | 7.40 |
| 32 | 6.33 | 7.00 | 7.33 | 7.33 | 7.67 | 7.00 | 7.00 | 6.16 |
| 33 | 5.00 | 5.00 | 5.67 | 6.00 | 6.33 | 5.00 | 5.33 | 5.22 |
| 34 | 4.33 | 4.33 | 5.00 | 5.00 | 6.00 | 5.00 | 6.00 | 4.73 |
| 35 | 5.33 | 5.33 | 6.00 | 6.33 | 6.00 | 4.67 | 5.33 | 5.47 |
| 36 | 7.00 | 7.67 | 8.67 | 8.67 | 8.67 | 7.67 | 7.33 | 7.16 |
| 37 | 6.67 | 6.33 | 6.67 | 7.00 | 7.00 | 6.67 | 6.00 | 6.29 |
| 38 | 6.67 | 7.33 | 7.67 | 8.00 | 8.00 | 7.67 | 7.00 | 6.89 |
| 39 | 8.00 | 8.67 | 8.67 | 9.00 | 8.33 | 8.00 | 7.33 | 7.73 |
| 40 | 7.00 | 7.33 | 7.67 | 7.67 | 8.00 | 7.67 | 7.00 | 6.80 |
| 41 | 6.67 | 7.33 | 7.67 | 8.33 | 7.67 | 7.67 | 7.00 | 6.96 |
| 42 | 6.67 | 7.00 | 7.33 | 8.00 | 8.00 | 7.00 | 6.67 | 6.60 |
| 43 | 8.00 | 8.33 | 8.33 | 8.67 | 8.33 | 8.00 | 7.00 | 7.49 |
| 44 | 5.33 | 5.67 | 6.00 | 6.33 | 6.67 | 5.33 | 5.67 | 5.73 |
| 45 | 3.67 | 3.67 | 4.33 | 4.33 | 4.67 | 4.00 | 5.33 | 3.80 |
| 46 | 7.00 | 7.00 | 7.33 | 8.00 | 7.67 | 7.33 | 7.00 | 6.84 |
| 47 | 1.00 | 1.00 | 1.00 | 1.00 | 5.00 | 6.33 | 7.67 | 2.46 |
| LSD (P = 0.05) | 1.17 | 1.00 | 0.90 | 0.77 | 0.86 | 0.87 | 0.70 | 0.25 |
| CV % | 11 | 9 | 8 | 7 | 7 | 8 | 6 | 10 |

TABLE 15

Quality estimates after overseeding Patriot bermudagrass on 15 October. Turf quality based on a 1-9 scale, where 1 = dead grass, 5 = minimally acceptable quality, and 9 = highest quality

| Turfgrass | 28 | 42 | 56 | 70 | 84 | 98 | 112 | 126 | 140 |
|---|---|---|---|---|---|---|---|---|---|
| 1 | 5.00 | 5.67 | 6.33 | 7.00 | 7.33 | 6.67 | 7.33 | 7.00 | 7.33 |
| 2 | 4.67 | 4.67 | 5.33 | 6.33 | 7.00 | 6.00 | 6.67 | 5.67 | 6.00 |
| 3 | 4.67 | 5.33 | 6.00 | 6.33 | 6.67 | 6.33 | 6.33 | 6.33 | 6.33 |
| 4 | 3.00 | 4.00 | 4.33 | 5.33 | 5.67 | 4.33 | 5.67 | 5.33 | 5.00 |
| 5 | 5.33 | 6.00 | 6.67 | 7.00 | 7.33 | 7.00 | 7.33 | 7.33 | 7.33 |
| 6 | 3.33 | 4.00 | 5.00 | 5.33 | 5.67 | 5.00 | 5.33 | 5.00 | 5.00 |
| 7 | 3.67 | 4.67 | 5.67 | 6.33 | 6.67 | 5.67 | 5.67 | 5.67 | 5.67 |
| 8 | 4.67 | 5.67 | 6.00 | 6.67 | 7.00 | 6.33 | 6.67 | 6.67 | 6.67 |
| 9 | 3.67 | 4.67 | 5.33 | 6.33 | 6.67 | 6.33 | 6.67 | 6.00 | 5.67 |
| 10 | 3.33 | 4.67 | 5.67 | 6.33 | 6.67 | 5.33 | 6.00 | 5.67 | 5.67 |
| 11 | 3.67 | 4.67 | 5.33 | 5.67 | 5.67 | 5.00 | 5.67 | 5.33 | 5.67 |
| 12 | 4.33 | 4.67 | 5.67 | 6.00 | 6.33 | 5.67 | 6.33 | 6.33 | 6.33 |
| 13 | 3.00 | 3.67 | 4.67 | 5.67 | 5.67 | 4.67 | 5.67 | 5.33 | 5.33 |
| 14 | 4.33 | 4.67 | 5.00 | 5.00 | 5.00 | 4.33 | 4.67 | 4.67 | 4.67 |
| 15 | 3.67 | 4.00 | 4.67 | 5.00 | 5.33 | 5.00 | 5.00 | 5.00 | 5.00 |
| 16 | 3.00 | 3.33 | 4.33 | 4.33 | 4.33 | 3.33 | 3.33 | 3.33 | 4.00 |
| 17 | 5.00 | 5.33 | 6.33 | 6.33 | 6.67 | 6.00 | 6.00 | 6.00 | 6.33 |
| 18 | 4.00 | 5.00 | 5.67 | 6.33 | 6.67 | 6.33 | 7.00 | 6.67 | 6.67 |
| 19 | 5.33 | 6.33 | 7.33 | 7.33 | 7.33 | 7.00 | 7.33 | 7.33 | 7.67 |
| 20 | 5.00 | 6.33 | 6.67 | 7.00 | 7.00 | 6.00 | 6.67 | 6.00 | 6.00 |
| 21 | 5.00 | 5.67 | 6.67 | 6.67 | 7.00 | 6.00 | 7.00 | 6.33 | 6.33 |
| 22 | 5.00 | 5.67 | 6.00 | 6.33 | 6.67 | 5.67 | 5.67 | 5.67 | 5.67 |
| 23 | 3.33 | 4.33 | 5.33 | 6.00 | 6.67 | 5.67 | 6.33 | 5.67 | 6.00 |
| 24 | 4.33 | 5.00 | 5.33 | 5.67 | 5.67 | 4.67 | 5.00 | 5.00 | 5.00 |
| 25 | 4.33 | 4.67 | 5.67 | 6.00 | 6.33 | 5.67 | 6.33 | 5.67 | 6.00 |
| 26 | 4.33 | 5.67 | 6.00 | 6.33 | 6.33 | 5.33 | 6.33 | 6.33 | 6.33 |
| 27 | 3.33 | 3.67 | 4.67 | 5.33 | 5.33 | 4.00 | 5.00 | 4.33 | 4.33 |
| 28 | 3.67 | 4.67 | 5.67 | 6.33 | 6.67 | 4.67 | 5.33 | 5.00 | 5.67 |
| 29 | 3.33 | 3.67 | 4.67 | 5.33 | 6.00 | 5.00 | 5.33 | 5.00 | 5.33 |
| 30 | 4.00 | 5.67 | 6.33 | 7.33 | 7.33 | 7.00 | 7.00 | 7.00 | 7.33 |
| 31 | 3.67 | 4.67 | 5.33 | 5.67 | 6.00 | 5.33 | 5.67 | 5.00 | 5.00 |
| 32 | 3.00 | 3.67 | 4.00 | 4.67 | 5.00 | 4.67 | 4.67 | 4.00 | 4.33 |
| 33 | 4.00 | 4.00 | 5.33 | 5.67 | 5.67 | 4.33 | 5.33 | 4.67 | 5.00 |
| 34 | 3.33 | 4.00 | 4.33 | 5.00 | 5.67 | 4.00 | 4.33 | 4.33 | 4.33 |
| 35 | 3.33 | 4.00 | 5.00 | 6.00 | 6.67 | 5.33 | 5.67 | 5.33 | 5.67 |
| 36 | 3.67 | 3.67 | 4.33 | 5.00 | 5.67 | 4.67 | 4.67 | 4.33 | 4.67 |
| 37 | 4.00 | 4.67 | 4.67 | 5.67 | 6.33 | 5.67 | 6.33 | 6.00 | 6.33 |
| 38 | 4.33 | 5.00 | 5.33 | 5.67 | 6.33 | 6.00 | 6.33 | 6.33 | 6.00 |
| 39 | 3.67 | 4.33 | 5.33 | 6.00 | 6.33 | 6.00 | 6.33 | 6.00 | 6.33 |
| 40 | 4.33 | 5.00 | 5.33 | 5.33 | 6.33 | 6.33 | 6.33 | 5.67 | 6.00 |
| 41 | 4.67 | 5.33 | 5.67 | 6.33 | 6.67 | 5.67 | 6.00 | 6.00 | 5.67 |
| 42 | 4.33 | 5.00 | 5.33 | 5.67 | 6.33 | 5.67 | 6.00 | 5.33 | 5.67 |

TABLE 15-continued

Quality estimates after overseeding Patriot bermudagrass on 15 October. Turf quality based on a 1-9 scale, where 1 = dead grass, 5 = minimally acceptable quality, and 9 = highest quality

| Turfgrass | Turfgrass Quality Estimates at Day | | | | | | | |
|---|---|---|---|---|---|---|---|---|
| | 28 | 42 | 56 | 70 | 84 | 98 | 112 | 126 | 140 |
| 43 | 4.00 | 5.00 | 5.67 | 6.33 | 7.00 | 6.33 | 6.33 | 6.00 | 6.00 |
| 44 | 3.67 | 4.33 | 5.33 | 5.67 | 6.67 | 4.67 | 5.67 | 5.33 | 5.33 |
| 45 | 3.33 | 3.33 | 3.67 | 4.00 | 4.00 | 2.67 | 3.00 | 3.00 | 3.67 |
| 46 | 5.33 | 5.33 | 6.00 | 6.67 | 7.00 | 6.00 | 6.33 | 6.00 | 6.33 |
| 47 | 6.33 | 3.33 | 1.33 | 1.33 | 1.33 | 1.00 | 1.00 | 1.00 | 1.00 |
| LSD (P = 0.05) | 1.17 | 1.41 | 1.43 | 1.59 | 1.40 | 1.24 | 1.41 | 1.39 | 1.50 |
| CV % | 18 | 19 | 17 | 17 | 14 | 14 | 15 | 16 | 17 |

TABLE 16

Quality estimates after overseeding Patriot bermudagrass on 15 October. Turf quality based on a 1-9 scale, where 1 = dead grass, 6 = minimally acceptable quality, and 9 = highest quality

| Turfgrass | Turfgrass Quality Estimates at Day | | | | | | | Season Mean |
|---|---|---|---|---|---|---|---|---|
| | 154 | 168 | 182 | 196 | 210 | 224 | 238 | |
| 1 | 7.67 | 7.67 | 8.00 | 8.33 | 8.67 | 8.00 | 8.00 | 7.25 |
| 2 | 6.00 | 7.00 | 7.33 | 8.00 | 8.33 | 8.00 | 8.00 | 6.56 |
| 3 | 6.33 | 7.00 | 7.67 | 8.33 | 8.67 | 8.00 | 8.00 | 6.77 |
| 4 | 4.33 | 4.33 | 5.00 | 6.00 | 6.00 | 6.33 | 7.00 | 5.10 |
| 5 | 7.67 | 7.67 | 7.67 | 8.00 | 8.00 | 7.33 | 7.67 | 7.21 |
| 6 | 5.33 | 5.33 | 6.33 | 6.67 | 7.00 | 6.67 | 7.00 | 5.50 |
| 7 | 5.67 | 5.67 | 6.33 | 7.00 | 6.67 | 7.00 | 6.00 | 5.88 |
| 8 | 6.67 | 7.00 | 7.00 | 7.67 | 8.00 | 7.67 | 8.00 | 6.77 |
| 9 | 6.33 | 6.67 | 7.33 | 8.00 | 8.00 | 7.67 | 7.67 | 6.44 |
| 10 | 6.00 | 6.00 | 6.33 | 6.67 | 6.67 | 6.67 | 6.67 | 5.90 |
| 11 | 6.00 | 6.33 | 6.67 | 7.33 | 7.00 | 7.00 | 7.00 | 5.88 |
| 12 | 6.00 | 6.00 | 6.33 | 6.33 | 6.67 | 7.00 | 7.00 | 6.06 |
| 13 | 5.33 | 5.67 | 6.00 | 6.33 | 6.67 | 6.00 | 6.67 | 5.40 |
| 14 | 5.00 | 5.33 | 6.00 | 6.67 | 7.33 | 7.00 | 7.67 | 5.46 |
| 15 | 5.67 | 6.67 | 7.00 | 8.00 | 8.67 | 8.00 | 8.00 | 5.92 |
| 16 | 4.67 | 5.67 | 6.00 | 6.33 | 7.00 | 7.33 | 8.00 | 4.90 |
| 17 | 6.67 | 6.67 | 7.33 | 7.67 | 8.33 | 8.00 | 8.00 | 6.67 |
| 18 | 7.67 | 8.00 | 8.33 | 8.33 | 8.67 | 8.00 | 8.00 | 6.98 |
| 19 | 8.00 | 8.00 | 9.00 | 9.00 | 9.00 | 8.33 | 9.00 | 7.65 |
| 20 | 6.67 | 7.00 | 7.33 | 7.33 | 8.00 | 7.67 | 7.67 | 6.77 |
| 21 | 6.67 | 7.00 | 7.00 | 7.67 | 8.33 | 8.00 | 8.00 | 6.83 |
| 22 | 5.67 | 6.67 | 7.33 | 8.00 | 8.67 | 7.67 | 7.67 | 6.50 |
| 23 | 6.67 | 7.67 | 8.00 | 8.33 | 9.00 | 8.00 | 7.67 | 6.54 |
| 24 | 5.33 | 5.67 | 6.67 | 7.33 | 8.00 | 7.67 | 7.67 | 5.88 |
| 25 | 6.00 | 6.33 | 7.33 | 7.33 | 8.33 | 8.00 | 8.00 | 6.38 |
| 26 | 6.67 | 7.00 | 7.67 | 8.00 | 8.33 | 7.67 | 8.00 | 6.65 |
| 27 | 4.67 | 5.00 | 5.33 | 5.67 | 6.00 | 6.00 | 7.00 | 4.98 |
| 28 | 5.67 | 6.00 | 6.33 | 6.67 | 6.33 | 5.67 | 6.33 | 5.67 |
| 29 | 5.67 | 6.00 | 7.00 | 7.33 | 8.00 | 8.00 | 8.00 | 5.85 |
| 30 | 7.67 | 8.00 | 8.33 | 8.67 | 9.00 | 8.00 | 8.00 | 7.29 |
| 31 | 6.00 | 7.00 | 7.33 | 8.00 | 8.33 | 7.67 | 7.67 | 6.15 |
| 32 | 5.33 | 6.00 | 6.33 | 7.00 | 7.33 | 7.67 | 8.00 | 5.35 |
| 33 | 5.00 | 5.33 | 6.00 | 6.33 | 6.67 | 6.33 | 6.33 | 5.38 |
| 34 | 4.00 | 4.33 | 6.00 | 6.00 | 6.00 | 6.00 | 6.67 | 4.90 |
| 35 | 5.67 | 6.33 | 6.33 | 7.00 | 6.67 | 6.33 | 6.67 | 5.75 |
| 36 | 5.33 | 6.33 | 6.67 | 7.33 | 8.33 | 7.67 | 8.00 | 5.65 |
| 37 | 6.33 | 6.33 | 6.67 | 7.33 | 7.33 | 7.00 | 7.00 | 6.10 |
| 38 | 6.00 | 6.33 | 6.67 | 7.33 | 8.00 | 7.67 | 8.00 | 6.33 |
| 39 | 6.67 | 7.33 | 7.67 | 8.33 | 9.00 | 8.00 | 8.00 | 6.58 |
| 40 | 6.33 | 7.00 | 7.33 | 8.33 | 8.33 | 8.00 | 8.00 | 6.50 |
| 41 | 6.00 | 6.67 | 7.67 | 8.00 | 8.00 | 8.00 | 8.00 | 6.52 |
| 42 | 6.33 | 6.67 | 7.33 | 7.67 | 8.33 | 8.00 | 8.00 | 6.35 |
| 43 | 7.00 | 7.00 | 8.00 | 8.67 | 8.67 | 8.33 | 8.00 | 6.77 |
| 44 | 5.67 | 6.00 | 6.67 | 6.67 | 7.00 | 6.67 | 7.00 | 5.77 |
| 45 | 3.67 | 4.00 | 4.67 | 4.67 | 4.67 | 4.67 | 5.67 | 3.92 |
| 46 | 6.33 | 6.67 | 7.33 | 7.33 | 8.00 | 7.67 | 7.67 | 6.63 |
| 47 | 1.00 | 1.00 | 1.00 | 1.00 | 4.67 | 5.67 | 7.33 | 2.46 |
| LSD (P = 0.05) | 1.44 | 1.27 | 1.07 | 0.97 | 0.82 | 0.69 | 0.72 | 0.30 |
| CV % | 15 | 12 | 10 | 8 | 7 | 6 | 6 | 12 |

TABLE 17

Bermudagrass coverage estimates after overseeding Patriot bermudagrass on 15 October Bermudagrass Coverage at Day

| Turfgrass | 210 | 224 | 238 |
|---|---|---|---|
| 1 | 8.33 | 41.67 | 51.67 |
| 2 | 16.67 | 45.00 | 58.33 |
| 3 | 15.00 | 46.67 | 60.00 |
| 4 | 25.00 | 60.00 | 91.67 |
| 5 | 18.33 | 58.33 | 63.33 |
| 6 | 16.67 | 63.33 | 85.00 |
| 7 | 16.67 | 58.33 | 73.33 |
| 8 | 16.67 | 51.67 | 60.00 |
| 9 | 10.00 | 48.33 | 61.67 |
| 10 | 16.67 | 60.00 | 78.33 |
| 11 | 20.00 | 56.67 | 80.00 |
| 12 | 21.67 | 71.67 | 78.33 |
| 13 | 21.67 | 71.67 | 93.33 |
| 14 | 21.67 | 66.67 | 73.33 |
| 15 | 16.67 | 66.67 | 85.00 |
| 16 | 25.00 | 73.33 | 91.67 |
| 17 | 18.33 | 60.00 | 65.00 |
| 18 | 15.00 | 53.33 | 66.67 |
| 19 | 10.00 | 48.33 | 51.67 |
| 20 | 18.33 | 61.67 | 70.00 |
| 21 | 13.33 | 51.67 | 65.00 |
| 22 | 18.33 | 48.33 | 70.00 |
| 23 | 11.67 | 61.67 | 78.33 |
| 24 | 20.00 | 68.33 | 78.33 |
| 25 | 11.67 | 50.00 | 66.67 |
| 26 | 18.33 | 56.67 | 66.67 |
| 27 | 21.67 | 58.33 | 83.33 |
| 28 | 20.00 | 56.67 | 78.33 |
| 29 | 16.67 | 46.67 | 66.67 |
| 30 | 8.33 | 35.00 | 51.67 |
| 31 | 13.33 | 53.33 | 68.33 |
| 32 | 16.67 | 63.33 | 78.33 |
| 33 | 23.33 | 60.00 | 88.33 |
| 34 | 33.33 | 75.00 | 91.67 |
| 35 | 18.33 | 60.00 | 83.33 |
| 36 | 20.00 | 63.33 | 78.33 |

TABLE 17-continued

Bermudagrass coverage estimates after overseeding Patriot bermudagrass on 15 October Bermudagrass Coverage at Day

| Turfgrass | 210 | 224 | 238 |
|---|---|---|---|
| 37 | 11.67 | 51.67 | 70.00 |
| 38 | 16.67 | 56.67 | 78.33 |
| 39 | 11.67 | 53.33 | 63.33 |
| 40 | 21.67 | 61.67 | 78.33 |
| 41 | 13.33 | 48.33 | 61.67 |
| 42 | 18.33 | 60.00 | 73.33 |
| 43 | 11.67 | 40.00 | 56.67 |
| 44 | 16.67 | 63.33 | 91.67 |
| 45 | 30.00 | 63.33 | 91.67 |
| 46 | 11.67 | 50.00 | 66.67 |
| 47 | 66.67 | 85.00 | 98.33 |
| LSD (P = 0.05) | 8.91 | 18.58 | 18.92 |
| CV % | 30 | 20 | 15 |

TABLE 18

Texture (1 to 9 scale), shear strength (N m force), and density (1 to 9 scale) ratings after over seeding Patriot bermudagrass on 15 October

| Turfgrass | Texture Day 168 | Shear Strength Day 168 | Density Day 168 |
|---|---|---|---|
| 1 | 9.00 | 120.00 | 9.00 |
| 2 | 9.00 | 111.00 | 8.33 |
| 3 | 9.00 | 112.33 | 8.00 |
| 4 | 5.67 | 115.00 | 5.67 |
| 5 | 9.00 | 118.33 | 8.00 |
| 6 | 7.33 | 108.67 | 7.33 |
| 7 | 7.67 | 120.67 | 7.67 |
| 8 | 9.00 | 115.00 | 8.33 |
| 9 | 9.00 | 128.33 | 8.00 |
| 10 | 8.00 | 110.00 | 7.33 |
| 11 | 8.00 | 119.33 | 7.67 |
| 12 | 7.67 | 127.00 | 7.67 |
| 13 | 7.33 | 113.00 | 6.67 |
| 14 | 8.67 | 102.00 | 7.33 |
| 15 | 9.00 | 109.67 | 7.67 |
| 16 | 8.67 | 109.00 | 7.67 |
| 17 | 9.00 | 114.00 | 8.33 |
| 18 | 9.00 | 109.33 | 8.67 |
| 19 | 9.00 | 117.67 | 8.67 |
| 20 | 9.00 | 126.33 | 8.33 |
| 21 | 9.00 | 117.67 | 8.00 |
| 22 | 9.00 | 116.00 | 8.33 |
| 23 | 9.00 | 125.00 | 8.67 |
| 24 | 9.00 | 118.67 | 8.00 |
| 25 | 9.00 | 110.33 | 8.33 |
| 26 | 9.00 | 119.00 | 8.00 |
| 27 | 6.67 | 112.00 | 6.33 |
| 28 | 7.00 | 115.67 | 6.67 |
| 29 | 9.00 | 116.67 | 7.67 |
| 30 | 9.00 | 118.00 | 8.67 |
| 31 | 9.00 | 120.33 | 9.00 |
| 32 | 8.33 | 112.67 | 7.67 |
| 33 | 7.67 | 98.67 | 7.00 |
| 34 | 6.00 | 108.33 | 5.67 |
| 35 | 7.00 | 116.33 | 7.00 |
| 36 | 8.33 | 116.33 | 7.67 |
| 37 | 8.00 | 110.67 | 8.00 |
| 38 | 8.67 | 116.67 | 8.00 |
| 39 | 9.00 | 120.67 | 9.00 |
| 40 | 9.00 | 113.67 | 8.33 |
| 41 | 9.00 | 117.33 | 8.33 |
| 42 | 8.67 | 115.33 | 8.67 |
| 43 | 9.00 | 112.33 | 8.67 |
| 44 | 7.33 | 116.33 | 6.67 |
| 45 | 5.33 | 97.33 | 4.33 |
| 46 | 9.00 | 109.67 | 8.00 |
| 47 |  | 57.33 |  |
| LSD (P = 0.05) | 0.60 | 18.00 | 0.95 |
| CV % | 4 | 10 | 8 |

TABLE 19

Average color ratings based on digital image analysis (DGCI = Digital Green Color Index) estimates after overseeding Patriot bermudagrass on 15 October

| Turfgrass | 28 | 56 | 91 | 119 | 146 | 182 | 210 | Season Mean |
|---|---|---|---|---|---|---|---|---|
| 1 | 0.510 | 0.500 | 0.490 | 0.440 | 0.480 | 0.490 | 0.500 | 0.486 |
| 2 | 0.490 | 0.480 | 0.500 | 0.430 | 0.440 | 0.480 | 0.510 | 0.475 |
| 3 | 0.480 | 0.490 | 0.490 | 0.440 | 0.470 | 0.480 | 0.480 | 0.475 |
| 4 | 0.430 | 0.460 | 0.400 | 0.380 | 0.410 | 0.390 | 0.390 | 0.410 |
| 5 | 0.500 | 0.520 | 0.500 | 0.470 | 0.490 | 0.500 | 0.510 | 0.499 |
| 6 | 0.450 | 0.430 | 0.420 | 0.390 | 0.410 | 0.430 | 0.430 | 0.421 |
| 7 | 0.460 | 0.450 | 0.420 | 0.390 | 0.420 | 0.430 | 0.440 | 0.431 |
| 8 | 0.480 | 0.480 | 0.460 | 0.430 | 0.460 | 0.460 | 0.480 | 0.466 |
| 9 | 0.490 | 0.490 | 0.460 | 0.420 | 0.450 | 0.460 | 0.470 | 0.463 |
| 10 | 0.490 | 0.470 | 0.450 | 0.410 | 0.430 | 0.420 | 0.410 | 0.439 |
| 11 | 0.460 | 0.460 | 0.420 | 0.400 | 0.420 | 0.440 | 0.450 | 0.437 |
| 12 | 0.490 | 0.500 | 0.470 | 0.440 | 0.450 | 0.450 | 0.440 | 0.463 |
| 13 | 0.470 | 0.450 | 0.440 | 0.410 | 0.420 | 0.410 | 0.390 | 0.425 |
| 14 | 0.480 | 0.460 | 0.430 | 0.390 | 0.410 | 0.470 | 0.500 | 0.448 |
| 15 | 0.460 | 0.470 | 0.460 | 0.410 | 0.410 | 0.490 | 0.510 | 0.458 |
| 16 | 0.480 | 0.450 | 0.400 | 0.360 | 0.430 | 0.470 | 0.470 | 0.435 |
| 17 | 0.500 | 0.500 | 0.480 | 0.440 | 0.450 | 0.500 | 0.510 | 0.482 |
| 18 | 0.500 | 0.500 | 0.490 | 0.440 | 0.470 | 0.500 | 0.510 | 0.485 |
| 19 | 0.520 | 0.520 | 0.500 | 0.470 | 0.480 | 0.520 | 0.530 | 0.505 |
| 20 | 0.490 | 0.510 | 0.490 | 0.430 | 0.450 | 0.480 | 0.520 | 0.483 |
| 21 | 0.500 | 0.510 | 0.490 | 0.440 | 0.440 | 0.490 | 0.530 | 0.485 |
| 22 | 0.510 | 0.500 | 0.490 | 0.440 | 0.450 | 0.500 | 0.530 | 0.487 |
| 23 | 0.480 | 0.490 | 0.480 | 0.440 | 0.450 | 0.500 | 0.510 | 0.480 |
| 24 | 0.470 | 0.470 | 0.460 | 0.410 | 0.430 | 0.490 | 0.510 | 0.462 |
| 25 | 0.480 | 0.480 | 0.460 | 0.410 | 0.430 | 0.480 | 0.520 | 0.466 |
| 26 | 0.490 | 0.490 | 0.440 | 0.390 | 0.420 | 0.490 | 0.520 | 0.464 |
| 27 | 0.430 | 0.440 | 0.410 | 0.350 | 0.360 | 0.410 | 0.400 | 0.401 |
| 28 | 0.470 | 0.480 | 0.420 | 0.400 | 0.430 | 0.410 | 0.390 | 0.430 |
| 29 | 0.480 | 0.460 | 0.440 | 0.420 | 0.420 | 0.480 | 0.510 | 0.458 |
| 30 | 0.510 | 0.510 | 0.500 | 0.460 | 0.480 | 0.500 | 0.530 | 0.498 |
| 31 | 0.480 | 0.480 | 0.470 | 0.430 | 0.450 | 0.510 | 0.520 | 0.477 |
| 32 | 0.460 | 0.440 | 0.420 | 0.370 | 0.430 | 0.480 | 0.480 | 0.440 |
| 33 | 0.460 | 0.460 | 0.420 | 0.380 | 0.420 | 0.410 | 0.390 | 0.421 |
| 34 | 0.450 | 0.410 | 0.390 | 0.340 | 0.400 | 0.400 | 0.390 | 0.397 |
| 35 | 0.470 | 0.470 | 0.440 | 0.400 | 0.450 | 0.410 | 0.390 | 0.434 |
| 36 | 0.500 | 0.470 | 0.450 | 0.400 | 0.440 | 0.500 | 0.510 | 0.468 |
| 37 | 0.460 | 0.450 | 0.430 | 0.400 | 0.440 | 0.460 | 0.440 | 0.441 |
| 38 | 0.480 | 0.470 | 0.450 | 0.420 | 0.430 | 0.470 | 0.490 | 0.458 |
| 39 | 0.490 | 0.500 | 0.500 | 0.460 | 0.460 | 0.510 | 0.520 | 0.491 |
| 40 | 0.470 | 0.440 | 0.450 | 0.410 | 0.420 | 0.480 | 0.500 | 0.453 |
| 41 | 0.490 | 0.480 | 0.460 | 0.420 | 0.440 | 0.480 | 0.490 | 0.464 |
| 42 | 0.470 | 0.460 | 0.440 | 0.390 | 0.420 | 0.470 | 0.490 | 0.451 |
| 43 | 0.510 | 0.510 | 0.500 | 0.440 | 0.480 | 0.490 | 0.520 | 0.493 |
| 44 | 0.460 | 0.460 | 0.440 | 0.400 | 0.400 | 0.410 | 0.410 | 0.426 |
| 45 | 0.460 | 0.400 | 0.320 | 0.310 | 0.400 | 0.380 | 0.350 | 0.373 |
| 46 | 0.500 | 0.470 | 0.430 | 0.420 | 0.430 | 0.470 | 0.500 | 0.459 |
| 47 | 0.460 | 0.300 | 0.260 | 0.250 | 0.190 | 0.210 | 0.400 | 0.296 |
| LSD (P = 0.05) | 0.040 | 0.046 | 0.034 | 0.035 | 0.049 | 0.020 | 0.025 | 0.014 |
| CV % | 5 | 6 | 5 | 5 | 7 | 3 | 3 | 5 |

Results and Discussion

Rate of establishment in the fairway/athletic field study varied between overseed grasses with the slowest average being Tetradark compared to PSAR-09-2 with a 50% faster establishment rate over the study period. The others in the fast establishing group at the top included Gulf, Carly, Allaire 3, HS-35, NAI-ALS5, and HS-36. Just considering the first month of growth, AMPT005 and Tetradark were the slowest to get started compared to Carly, Allaire 3, PSAR-09-2, HS-35 with a 29% greater rate.

In terms of average quality (density, color & texture) for the duration of the test, HS-35 came out on top, followed by followed by PPG-PR-303, SPR Overseeding Blend, and Cascadia. In terms of just color, Cascadia was the highest but similar to HS-35. The next group included PPG-PR-303, Man O'War, and NAI-P L2. Gulf had the lowest color rating.

Fine leaf texture is important to some for blending in with other grasses. Most of these grasses have a similar texture. Three grasses, Gulf, Approach, and PSAR-09-2 were rated as having coarser textures than the other grasses.

In situ shear strength data put Nomad 4 at the top (128 N m) and Gulf at the bottom (97 N m). This 24% drop is significant in terms of holding up under heavy cleat traffic or club divoting. It should be noted that adding an overseed increased shear strength on average by 95%.

The fastest bermudagrass regrowth were seen in plots growing PSAR-09-2, APMT005, CS-AR-106, and Gulf. With the exception of the American Ryegrass APMT005, these are all annual or intermediate ryegrasses.

Example 4—Drought Tolerance

Drought Stress Methods:
1. Establish turf trial
2. Keep soil saturation optimum for turf health
3. Starting in June: Withhold water (no irrigation during the duration of the stress)
4. Mow 3 times per week at 1.5"
5. Digital photos 24 hours after mowing
6. Use Digital Image Analysis to calculate the percent green cover
7. Study continues until top entry is reduced to 25% green cover
8. Analyzed using non-linear regression analysis with data fit to a sigmoid curve.

REFERENCES

Banfi, E., G. Galasso, B. Foggi, D. Kopeck & N. M. G. Ardenghi. 2017. *Schedonorus* and *Micropyropsis* to *Lolium* (Poaceae: Loliinae): New combinations and typifications. Taxon 66(3): 715 (23 Jun. 2017).

Ghesquiere, M., M. W. Humphreys, and S. Zwierzykowski. 2010. *Festulolium*. In. Fodder Crops and Amenity Grasses, Handbook of Plant Breeding. Eds. B. Boller, U.K. Posselt and F. Veronesi. Springer Science. 524 pp.

Hopkins, A. A., M. C. Saha and Z. Y. Wang. 2009. Chapter 19: Breeding, Genetics, and Cultivars. In Tall Fescue for the Twenty-first Century. Eds. H. A. Fribourg, D. B. Hannaway & C. P. West. Agronomy Monograph No. 53. ASA, CSSA, SSSA. Madison, Wis. USA. 539 pp.

DEPOSIT INFORMATION

A deposit of at least 25 packets with 25 seeds per packet of American ryegrass designated APMT005 has been made with the American Type Culture Collection (ATCC), Manassas, Va. 20110 USA, on 14 Feb. 2020. Those deposited seeds have been assigned ATCC Accession No. PTA-126634. The deposit was made in accordance with the terms and provision of the Budapest Treaty relating to the deposit of microorganisms and was made for a term of at least thirty (30) years and at least five (5) years after the most recent request for the furnishing of a sample of the deposit is received by the depository, or for the effective term of the patent, whichever is longer, and will be replaced if it becomes non-viable during that period.

The invention claimed is:
1. A seed of a hybrid grass plant variety designated APMT005, a sample of seed of said variety having been deposited under ATCC Accession Number PTA-126634.
2. A grass plant-produced by growing the seed of claim 1.
3. A grass plant having all the physiological and morphological characteristics of the grass plant of claim 2.

* * * * *